(12) United States Patent
Kimball et al.

(10) Patent No.: US 9,364,249 B2
(45) Date of Patent: Jun. 14, 2016

(54) METHOD AND APPARATUS FOR PROGRAMMING MODULAR SURGICAL INSTRUMENT

(75) Inventors: Cory G. Kimball, Cincinnati, OH (US);
Daniel W. Price, Loveland, OH (US);
William E. Clem, Bozeman, MT (US);
William D. Dannaher, Suzhou (CN);
Amy L. Marcotte, Mason, OH (US);
Timothy G. Dietz, Terrace Park, OH (US); Donna L. Korvick, Maineville, OH (US); Ashvani K. Madan, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 969 days.

(21) Appl. No.: 13/426,760

(22) Filed: Mar. 22, 2012

(65) Prior Publication Data
US 2013/0253499 A1 Sep. 26, 2013

(51) Int. Cl.
*A61B 18/04* (2006.01)
*A61B 17/32* (2006.01)
(Continued)

(52) U.S. Cl.
CPC ..... *A61B 17/320092* (2013.01); *A61B 18/1206* (2013.01); *A61B 19/44* (2013.01); *A61B 18/1442* (2013.01); *A61B 2017/0046* (2013.01); *A61B 2017/00221* (2013.01); *A61B 2017/00473* (2013.01); *A61B 2017/00477* (2013.01); *A61B 2017/2931* (2013.01); *A61B 2018/00642* (2013.01); *A61B 2018/00702* (2013.01);
(Continued)

(58) Field of Classification Search
CPC .................. A61B 17/320092; A61B 18/1206;
A61B 18/1442; A61B 19/44; A61B 2017/00473; A61B 2017/2931; A61B 2018/00642; A61B 2019/448
USPC ................................................ 606/34, 41, 42
See application file for complete search history.

(56) References Cited

U.S. PATENT DOCUMENTS

| 5,980,510 A | 11/1999 | Tsonton et al. |
| 6,500,176 B1 | 12/2002 | Truckai et al. |

(Continued)

FOREIGN PATENT DOCUMENTS

WO    WO 2010/039117    4/2010

OTHER PUBLICATIONS

U.S. Appl. No. 13/269,899, filed Oct. 10, 2011, Boudreaux et al.
(Continued)

*Primary Examiner* — Niketa Patel
*Assistant Examiner* — Lindsey G Hankins
(74) *Attorney, Agent, or Firm* — Frost Brown Todd LLC

(57) ABSTRACT

A surgical instrument operable to sever tissue includes a body assembly and a selectively coupleable end effector assembly. The end effector assembly may include a transmission assembly and an end effector. The body assembly includes a trigger and a casing having a distal aperture configured to receive a portion of the end effector assembly. First and second coupling mechanism portions cooperatively couple the end effector assembly to the body assembly for use. A cartridge positionable between the instrument and a generator includes information regarding operating parameters unique to the selectively coupleable end effector assembly and/or the desired surgical procedure, such as information regarding setting a maximum current set point within an ultrasonic transducer. The instrument is programmable with operating parameter information while within a sealed and sterilized packaging unit.

19 Claims, 15 Drawing Sheets

(51) Int. Cl.
*A61B 18/12* (2006.01)
*A61B 19/00* (2006.01)
*A61B 17/00* (2006.01)
*A61B 17/29* (2006.01)
*A61B 18/00* (2006.01)
*A61B 18/14* (2006.01)

(52) U.S. Cl.
CPC ......... *A61B2018/00791* (2013.01); *A61B 2018/00875* (2013.01); *A61B 2019/448* (2013.01)

(56) References Cited

U.S. PATENT DOCUMENTS

| | | |
|---|---|---|
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,416,101 B2 | 8/2008 | Shelton, IV et al. |
| 7,738,971 B2 | 6/2010 | Swayze et al. |
| 8,058,771 B2 | 11/2011 | Giordano et al. |
| 8,134,409 B2 | 3/2012 | Seki et al. |
| 8,246,608 B2 | 8/2012 | Omori et al. |
| 2004/0133189 A1* | 7/2004 | Sakurai ............... 606/1 |
| 2005/0165443 A1* | 7/2005 | Livneh ............... 606/205 |
| 2006/0079874 A1 | 4/2006 | Faller et al. |
| 2007/0060955 A1* | 3/2007 | Strother et al. ............... 607/2 |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0143797 A1 | 6/2009 | Smith et al. |
| 2009/0156958 A1 | 6/2009 | Mehta et al. |
| 2009/0209990 A1 | 8/2009 | Yates et al. |
| 2010/0069940 A1 | 3/2010 | Miller et al. |
| 2011/0015660 A1* | 1/2011 | Wiener et al. ............... 606/169 |
| 2011/0087212 A1 | 4/2011 | Aldridge et al. |
| 2011/0087218 A1 | 4/2011 | Boudreaux et al. |
| 2012/0078243 A1 | 3/2012 | Worrell et al. |
| 2012/0078247 A1 | 3/2012 | Worrell et al. |
| 2012/0116367 A1 | 5/2012 | Houser et al. |
| 2012/0116379 A1* | 5/2012 | Yates ............... A61B 17/00234 606/33 |
| 2012/0116388 A1 | 5/2012 | Houser et al. |
| 2012/0116396 A1 | 5/2012 | Price et al. |
| 2012/0210223 A1 | 8/2012 | Eppolito |

OTHER PUBLICATIONS

U.S. Appl. No. 61/410,603, filed Nov. 5, 2010, Houser.
EP Communication dated Nov. 19, 2013 for Application No. EP 13160483.
Extended European Search Report dated Jul. 18, 2013 for Application No. EP 13160483.
Partial European Search Report dated Jul. 18, 2013 for Application No. EP 13160483.
Chinese Office Action dated Mar. 2, 2016 for Application No. 201310093887.9, 4 pages.

* cited by examiner

METHOD AND APPARATUS FOR PROGRAMMING MODULAR SURGICAL INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Additional examples endoscopic surgical instruments include are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. patent application Ser. No. 13/151,481, entitled "Motor Driven Electrosurgical Device with Mechanical and Electrical Feedback," filed Jun. 2, 2011, published as U.S. Pat. Pub. No. 2012/0116379 on May 10, 2012, issued as U.S. Pat. No. 9,161,803 on Oct. 20, 2015, the disclosure of which is incorporated by reference herein; U.S. patent application Ser. No. 13/269,870, entitled "Surgical Instrument with Modular Shaft and End Effector," filed Oct. 10, 2011, published as U.S. Pat. Pub. No. 2012/0116388 on May 10, 2012, the disclosure of which is incorporated by reference herein; U.S. patent application Ser. No. 13/235,660, entitled "Articulation Joint Features for Articulating Surgical Device," filed Sep. 19, 2011, published as U.S. Pat. Pub. No. 2012/0078247 on Mar. 29, 2012, the disclosure of which is incorporated by reference herein; U.S. patent application Ser. No. 13/274,805, entitled "Surgical Instrument with Modular End Effector," filed Oct. 17, 2011, now U.S. Pat. No. 8,998,939, issued on Apr. 7, 2015, the disclosure of which is incorporated by reference herein; and U.S. patent application Ser. No. 13/276, 725, entitled "Medical Device Usage Data Processing," filed Oct. 19, 2011, published as U.S. Pat. Pub. No. 2012/0116367 on May 10, 2012, issued as U.S. Pat. No. 9,095,346 on Aug. 4, 2015, the disclosure of which is incorporated by reference herein.

In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
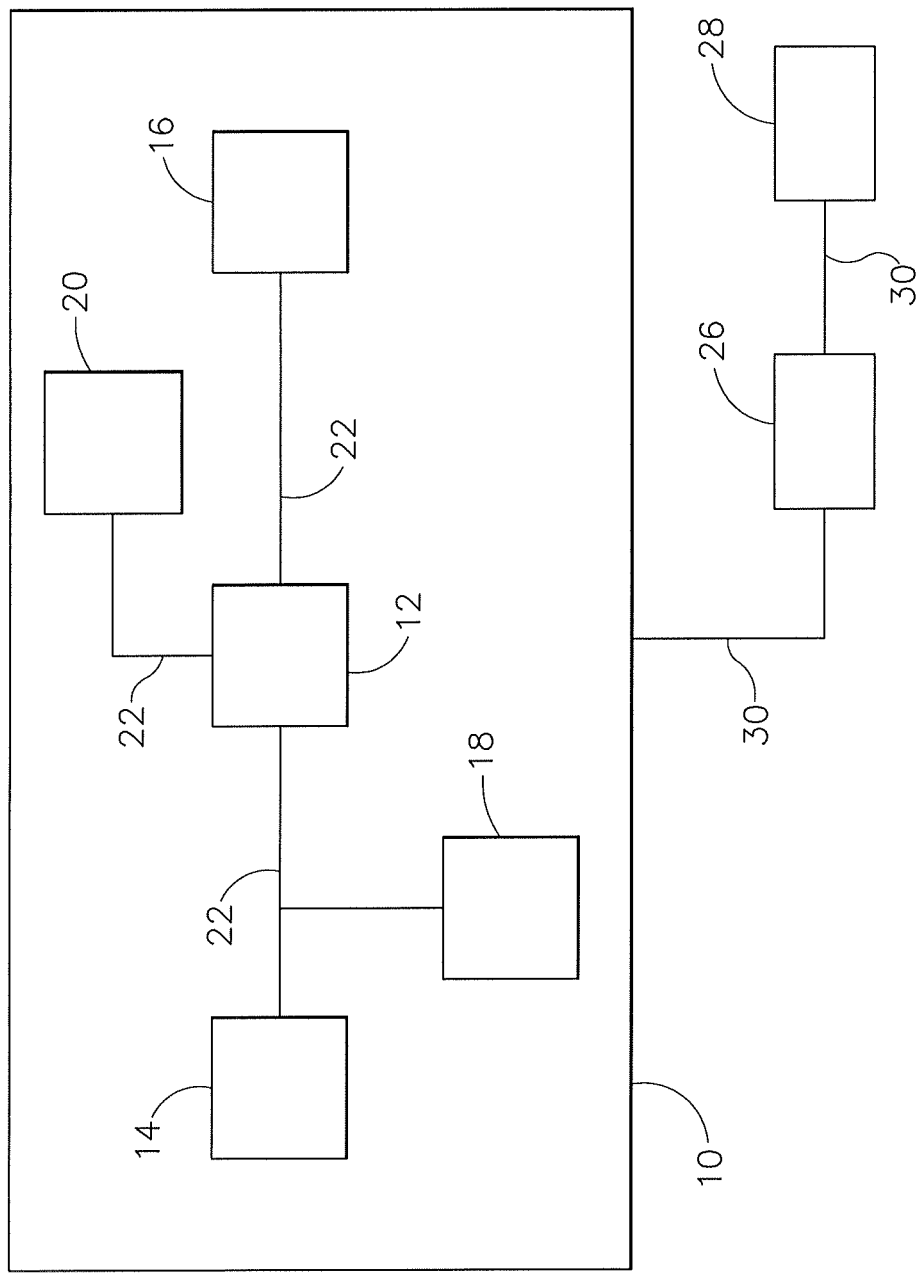
FIG. 1 depicts a schematic view of an exemplary surgical system comprising a medical device having a power source and a cartridge.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should be understood that the teachings below may be readily applied to any of the references that are cited herein. Various suitable ways in which the below teachings may be combined with the references cited herein will be apparent to those of ordinary skill in the art.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Surgical Instrument

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein and as described with respect to FIGS. 3A-3B below. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing impedance in tissue at end effector (16), sensing a temperature at end effector (16), determining movement and/or orientation of end effector (16), or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired. Sensor (20) of medical device (10) may be operable in accordance with the teachings of U.S. patent application Ser. No. 13/276,725, published as U.S. Pat. Pub. No. 2012/0016367 on May 10, 2012, issued as U.S. Pat. No. 9,095,346 on Aug. 4, 2015, the disclosure of which is incorporated by reference herein.

In some versions, a cartridge (26) and generator (28) are attached to medical device (10) via cable (30). For instance, generator (28) may serve as a substitute for power source (14). While medical device (10) is shown as being in communication with both cartridge (26) and generator (28) via cables (30), it should be understood that medical device (10) may alternatively communicate with one or both of cartridge (26) and generator (28) via a wireless communication.

II. Overview of Exemplary Ultrasonic Surgical System

Figure 2:
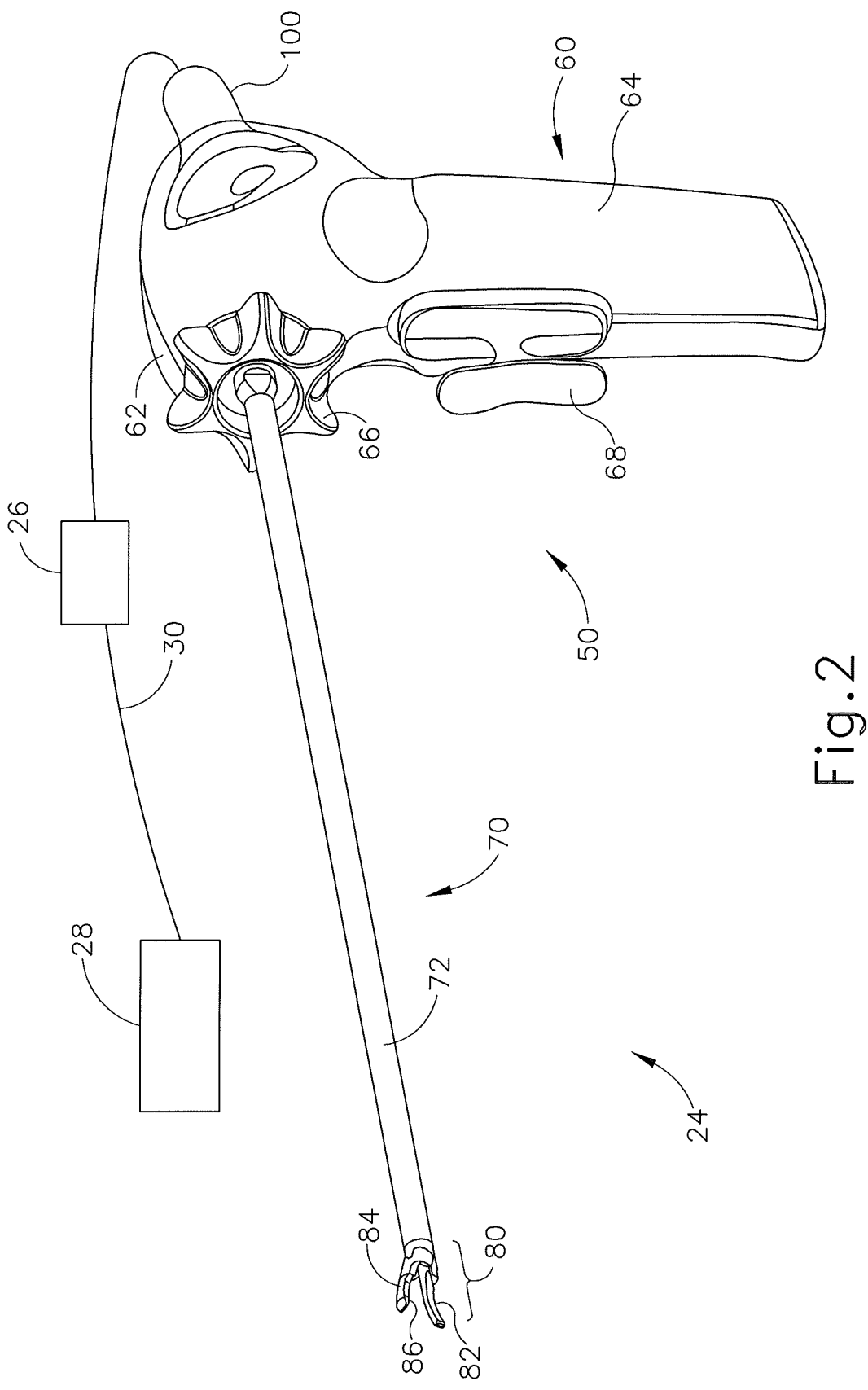
FIG. 2 depicts a perspective view of an exemplary ultrasonic surgical system comprising a surgical instrument and a generator.

FIG. 2 depicts a merely exemplary form that medical device (10) may take. FIG. 2 shows an exemplary ultrasonic surgical system (24) comprising an ultrasonic surgical instrument (50), a cartridge (26), a generator (28), and a cable (30) operable to couple generator (28) to surgical instrument (50). A suitable generator (28) is the GEN 300 sold by Ethicon Endo-Surgery, Inc. of Cincinnati, Ohio. By way of example only, generator (28) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302 issued on Mar. 24, 2015, and U.S. patent application Ser. No. 13/269,870, entitled "Surgical Instrument with Modular Shaft and End Effector," filed Oct. 10, 2011, published as U.S. Pat. Pub. No. 2012/0116388 on May 10, 2012, the disclosures of which are incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757 issued on Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture, described in more detail below, is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein. Toggle buttons (not shown) may be located on a distal surface of lower portion (64) and may be operable to activate transducer (100) at different operational levels using generator (28). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. No. 5,980,510; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744, issued Jun. 11, 2013; U.S. Pat. No. 6,500,176; U.S. Pat. Pub. No. 2011/0087218, now U.S. Pat. No. 8,939,974, issued Jan. 27, 2015; and/or U.S. Pat. Pub. No. 2009/0143797, now U.S. Pat. No. 8,419,757, issued Apr. 16, 2013. Additional optional configurations and features for surgical instrument (50) are described in U.S. patent application Ser. No. 13/269,899, entitled "Ultrasonic Surgical Instrument with Modular End Effector," filed on Oct. 10, 2011, issued as U.S. Pat. No. 9,050,125 on Jun. 9, 2015, the disclosure of which is incorporated by reference herein.

Figure 3A:
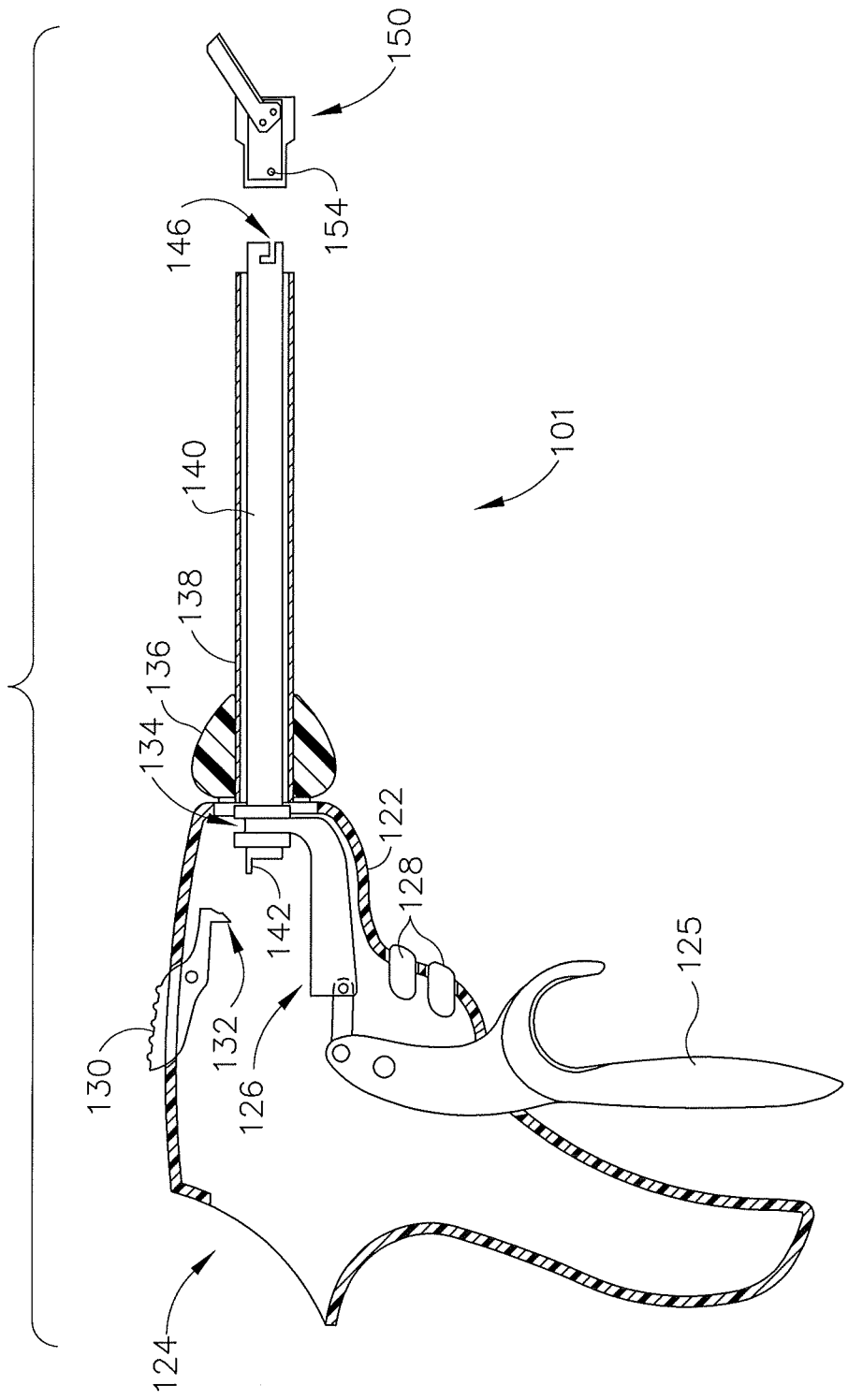
FIG. 3A depicts a perspective view of another exemplary surgical system comprising a surgical instrument with a transducer removed and a detachable end effector.
Figure 3B:
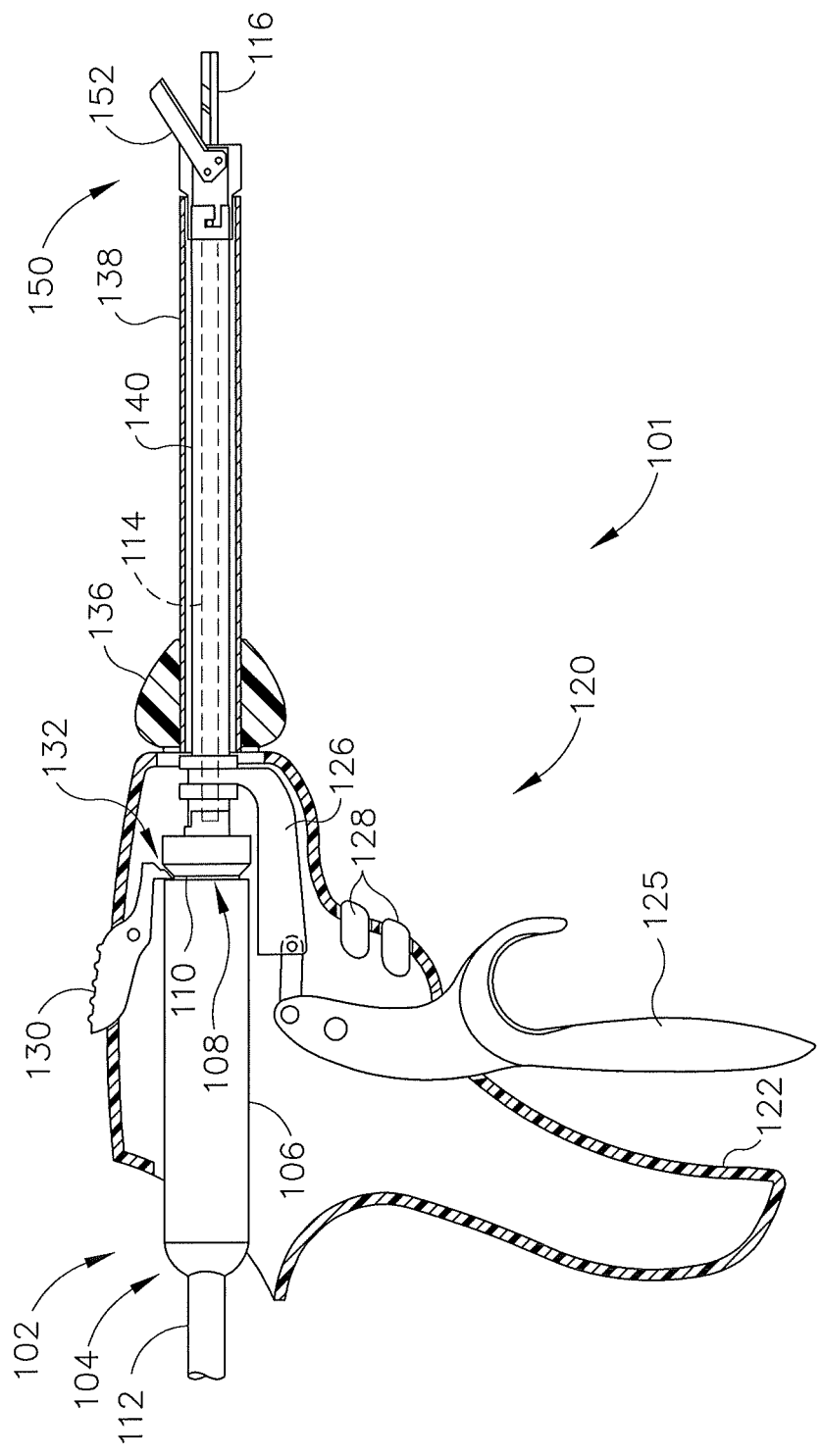
FIG. 3B depicts a perspective view of the surgical instrument of FIG. 3A with the transducer attached and the detachable end effector attached.

FIGS. 3A-3B depict an alternative version of an ultrasonic instrument (101) having a reusable transducer and blade assembly (102) for use in a handle assembly (120), and a detachable end effector (150). Transducer and blade assembly (102) comprises a transducer (104) and an elongated blade assembly coupled to transducer (104) and extending distally from transducer (104). Traducer (104) is operable to convert electrical power from cable (112) into ultrasonic vibrations at blade (116). Transducer (104) of the present example comprises a transducer body (106), a circumferential notch (108) formed in a distal end of transducer body (106), and a cable (112). Cable (112) of the present example is coupleable to a power source, such as generator (28) described above, to provide power to transducer (104). It should be understood that transducer (104) may be configured to omit cable (112), such as in a cordless transducer disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. Components of ultrasonic instrument (101) may be constructed and operable in accordance with the teachings of U.S. patent application Ser. No. 13/274,805, now U.S. Pat. No. 8,998,939, issued Apr. 7, 2015, which is incorporated by reference herein.

In the present example, casing (122) includes a proximal aperture (124) configured to receive transducer and blade assembly (102). Trigger (125) is pivotably coupled to casing (122) and is configured to pivot from an open position to a closed position. Trigger (125) is configured to actuate outer sheath (138) distally via an actuation assembly (126) when trigger (125) is in the closed position. Toggle buttons (128) comprise buttons operable to selectively activate transducer (104) at different operational levels using a power source and are operable in accordance with the teachings of U.S. patent application Ser. No. 13/274,805, now U.S. Pat. No. 8,998,939, issued Apr. 7, 2015, which is incorporated by reference herein.

Rotation knob (136) is rotatably coupled to a distal end of casing (122) and is coupled to outer sheath (138) and inner tubular actuation member (140) to rotate outer sheath (138) and inner tubular actuation member (140) relative to casing (122). In some versions, outer sheath (138) and inner tubular actuation member (140) are configured to selectively couple to rotation knob (136).

FIG. 3A shows casing (122) with a proximal aperture (124) configured to receive removable transducer and blade assembly (102). Instrument (101) is capable of accommodating various kinds of transducer and blade assemblies (102), including those with different types of transducer bodies (106) and/or those with different types of blades (116). End effector (150) is shown aligned with outer sheath (138) and inner tubular actuation member (140), but in a detached position. Initially the user inserts transducer and blade assembly (102) through proximal aperture (124). Assembly (102) is guided through inner tubular actuation member (140) and out through the distal end of inner tubular actuation member (140), as shown in FIG. 3B. When transducer and blade assembly (102) is fully inserted, latch member (130) engages notch (108) to retain transducer and blade assembly (102) longitudinally within handle assembly (120). Latch member (130), inner tubular actuation member (140), and transducer and blade assembly (102) may be constructed and operable in accordance with the teachings of U.S. patent application Ser. No. 13/274,805, issued as U.S. Pat. No. 8,998,939 on Apr. 7, 2015, which is incorporated by reference herein. It should be understood that transducer and blade assembly (102) can freely rotate relative to handle assembly (120) while still maintaining an electrical connection between electrical connector (132) and ring connector (110). In addition, as transducer and blade assembly (102) is inserted into handle assembly (120), a user may rotate transducer and blade assembly (102) and/or inner tubular actuation member (140) to align key (142) with a slot (not shown) of assembly (102). Such an alignment maintains the orientation between blade (116) and clamp arm (152) of end effector (150). In some versions, key (142) may be provided on waveguide (114) and/or blade (116) to align inner tubular actuation member (140) with waveguide (114) and/or blade (116). Of course, transducer and blade assembly (102) and/or components thereof may be removably coupled with casing (122) and other components of instrument (101) in numerous other ways as will be apparent to those of ordinary skill in the art in view of the teachings herein.

With transducer and blade assembly (102) axially restrained within handle assembly (120), end effector (150) of the present example is then attached to outer sheath (138) and inner tubular actuation member (140) as shown in FIG. 3B. It should be understood that instrument (101) is capable of accommodating various kinds of end effectors (150) as will be apparent to those of ordinary skill in the art in view of the teachings herein. Outer sheath (138) includes a circumferential groove (134) into which a portion of actuation assembly (126) is insertable. It should be understood that in some versions end effector (150) is coupled to outer sheath (138) and inner tubular actuation member (140) prior to the coupling of transducer and blade assembly (102). In the present example, opposing L-shaped slots (148) of inner tubular actuation member (140) and outer sheath (138) are aligned such that opposing bayonet pins (154) are insertable into longitudinal portions (143) of each L-shaped slot (148). When bayonet pins (154) reach the proximal end of longitudinal portions (143), the user rotates end effector (150) to rotate bayonet pins (154) into radial portions (144) until bayonet pins reach lock portions (146). With end effector (150) and transducer and blade assembly (102) coupled to handle assembly (120), the user may then use the surgical instrument for a procedure. Of course, end effector (150) and/or components thereof may be removably coupled with transducer and blade assembly (102) in numerous other ways as will be apparent to those of ordinary skill in the art in view of the teachings herein.

III. Overview of Exemplary Radiofrequency (RF) Surgical Instrument

Figure 4:
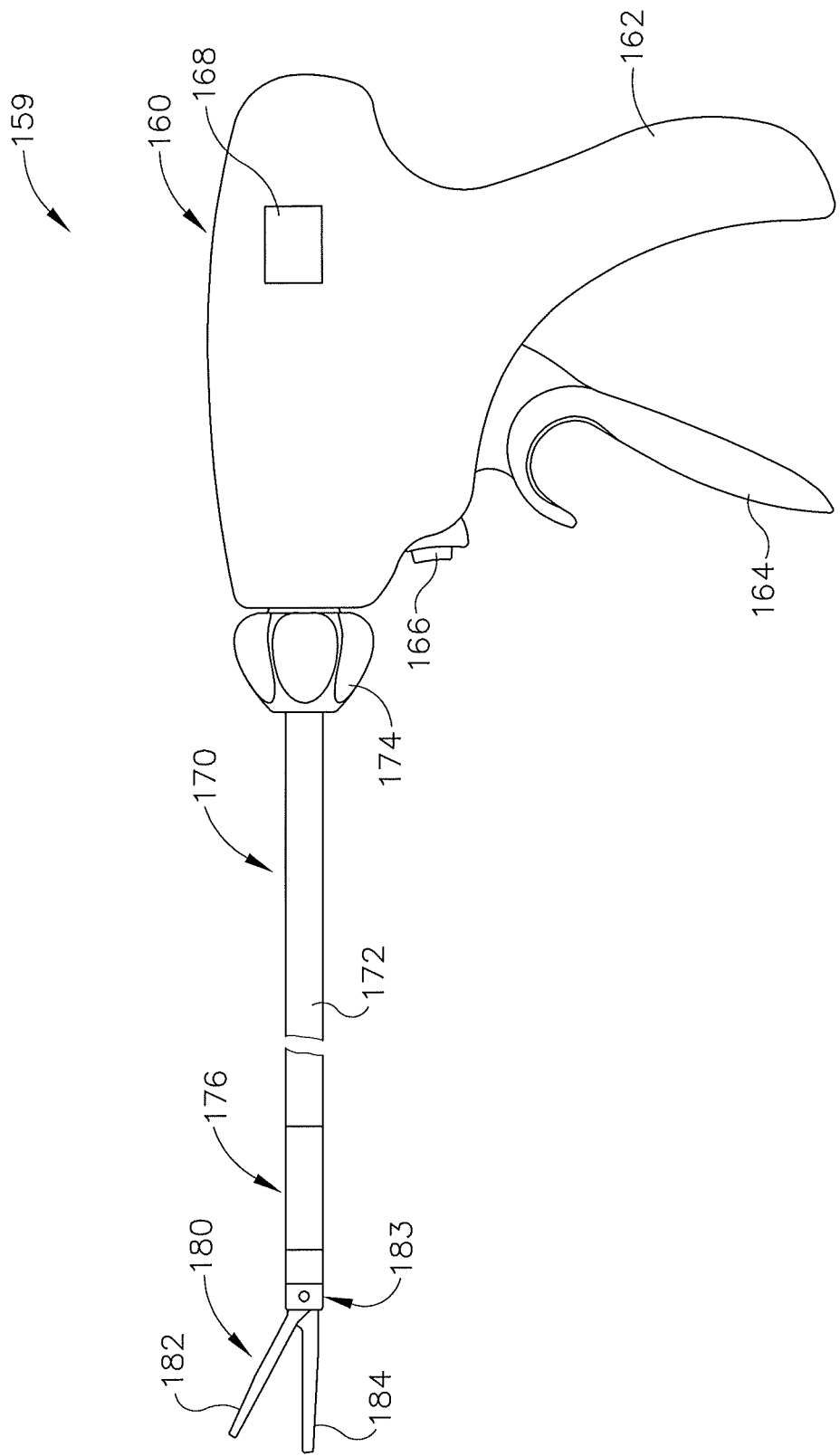
FIG. 4 depicts a side elevation view of an exemplary electrosurgical medical device.

While some surgical instruments are adapted to use ultrasonic energy to operate on tissue, other surgical instruments, such as surgical instrument (159), shown in FIGS. 3-4, can be configured to supply other kinds of energy, such as electrical energy and/or heat energy, to the tissue of a patient.

Figure 5:
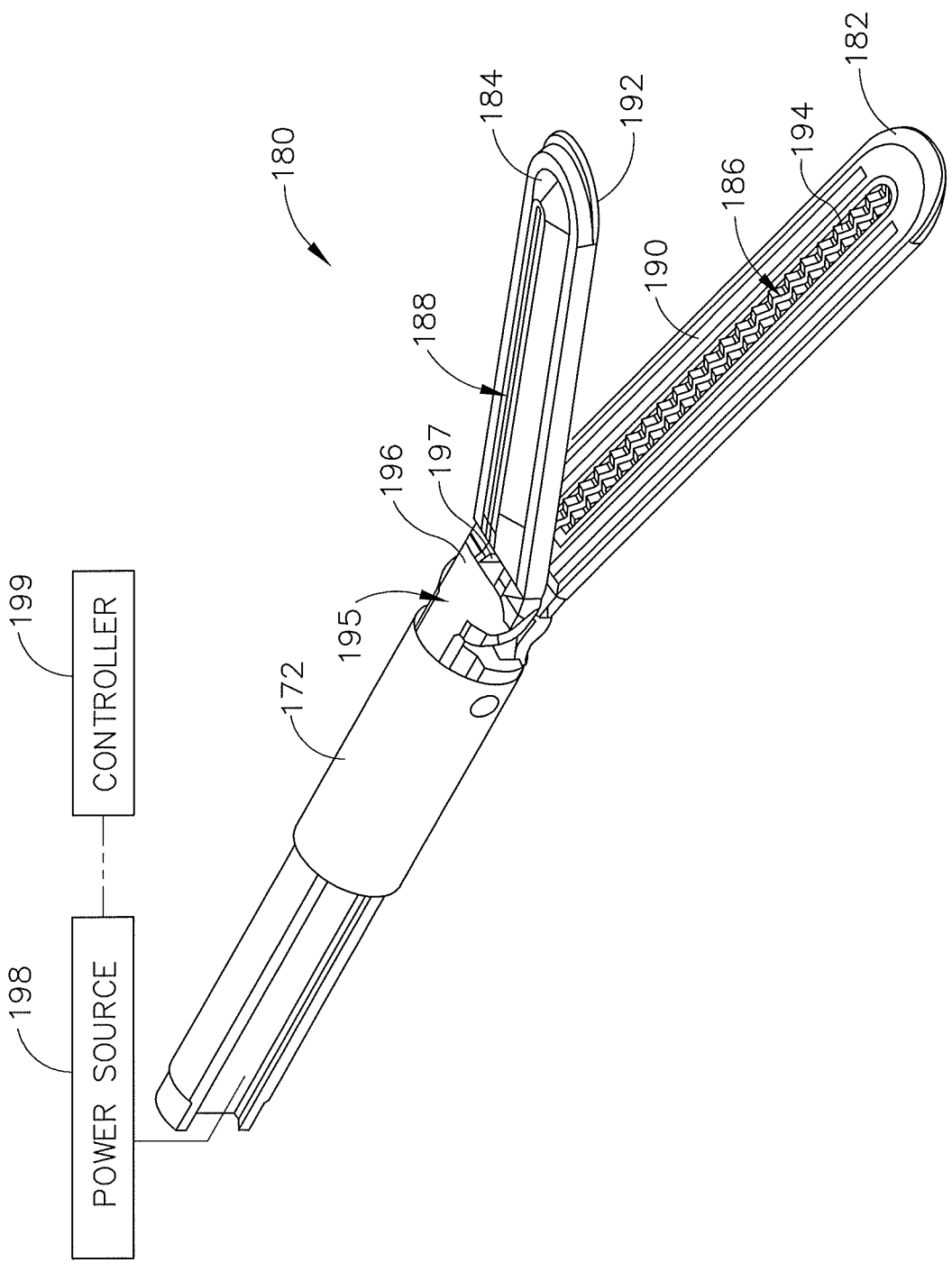
FIG. 5 depicts a perspective view of the end effector of the device of FIGS. 3A-3B, in an open configuration.

FIGS. 4-5 show an exemplary electrosurgical instrument (159) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974, issued Jan. 27, 2015; and/or U.S. patent application Ser. No. 13/151,481, published as U.S. Pat. Pub. No. 2012/0116379 on May 10, 2012, now U.S. Pat. No. 9,161,803. As described therein and as will be described in greater detail below, electrosurgical instrument (159) is operable to cut tissue and seal or weld tissue (e.g., a blood vessel, etc.) substantially simultaneously. In other words, electrosurgical instrument (159) operates similar to an endocutter type of stapler, except that electrosurgical instrument (159) provides tissue welding through application of bipolar RF energy instead of providing lines of staples to join tissue. It should also be understood that electrosurgical instrument (159) may have various structural and functional similarities with the ENSEAL® Tissue Sealing Device by Ethicon Endo-Surgery, Inc., of Cincinnati, Ohio. Furthermore, electrosurgical instrument (159) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (159), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (159) of the present example includes a handpiece (160), a shaft (170) extending distally from handpiece (160), and an end effector (180) disposed at a distal end of shaft (170). Handpiece (160) of the present example includes a pistol grip (162), a pivoting trigger (164), an activation button (166), and an articulation control (168). Trigger (164) is pivotable toward and away from pistol grip (162) to selectively actuate end effector (180) as will be described in greater detail below. Activation button (166) is operable to selectively activate RF circuitry that is in communication with end effector (180), in a manner described in U.S. patent application Ser. No. 13/235,660, published as U.S. Pat. Pub. No. 2012/0078247 on Mar. 29, 2012, and/or various other references that are cited and incorporated by reference herein. In some versions, activation button (166) also serves as a mechanical lockout against trigger (164), such that trigger (164) cannot be fully actuated unless button (166) is being pressed simultaneously. Examples of how such a lockout may be provided are disclosed in one or more of the references cited herein. It should be understood that pistol grip (162), trigger (164), and button (166) may be modified, substituted, supplemented, etc. in any suitable way, and that the descriptions of such components herein are merely illustrative. Articulation control (168) of the present example is operable to selectively control articulation section (176) of shaft (170) in a manner described in U.S. patent application Ser. No. 13/235,660, published as U.S. Pat. Pub. No. 2012/0078247 on Mar. 29, 2012, which is incorporated by reference herein.

Shaft (170) of the present example includes an outer sheath (172) and an articulation section (176). Articulation section (176) is operable to selectively position end effector (180) at various angles relative to the longitudinal axis defined by sheath (172). Various examples of forms that articulation section (176) and other components of shaft (170) may take are described in U.S. patent application Ser. No. 13/235,623, entitled "Control Features for Articulating Surgical Device," filed Sep. 19, 2011, published as U.S. Pat. Pub. No. 2012/0078243 on Mar. 29, 2012, the disclosure of which is incorporated by reference herein. For instance, it should be understood that various components that are operable to actuate articulation section (176) may extend through the interior of sheath (172). In some versions, shaft (170) is also rotatable about the longitudinal axis defined by sheath (172), relative to handpiece (160), via a knob (174). Such rotation may provide rotation of end effector (180) and shaft (170) unitarily. In some other versions, knob (174) is operable to rotate end effector (180) without rotating any portion of shaft (170) that is proximal of articulation section (176). As another merely illustrative example, electrosurgical instrument (159) may include one rotation control that provides rotatability of shaft (170) and end effector (180) as a single unit; and another rotation control that provides rotatability of end effector (180) without rotating any portion of shaft (170) that is proximal of articulation section (176). Other suitable rotation schemes will be apparent to those of ordinary skill in the art in view of the teachings herein. Of course, rotatable features may simply be omitted if desired.

B. Exemplary End Effector

End effector (180) of the present example comprises a first jaw (182) and a second jaw (184). In the present example, second jaw (184) is substantially fixed relative to shaft (170); while first jaw (182) pivots relative to shaft (170), toward and away from second jaw (184). In some versions, actuators such as rods or cables, etc., may extend through sheath (172) and be joined with first jaw (182) at a pivotal coupling (183), such that longitudinal movement of the actuator rods/cables/etc. through shaft (170) provides pivoting of first jaw (182) relative to shaft (170) and relative to second jaw (184). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (195), such that actuator rods/cables/etc. may simply be eliminated in some versions.

As best seen in FIGS. 4-5, first jaw (182) defines a longitudinally extending elongate slot (186); while second jaw (184) also defines a longitudinally extending elongate slot (148). In addition, the top side of first jaw (182) presents a first electrode surface (190); while the underside of second jaw (184) presents a second electrode surface (192). Electrode surfaces (190, 192) are in communication with an electrical source (198) via one or more conductors (not shown) that extend along the length of shaft (170). Electrical source (198) is operable to deliver RF energy to first electrode surface (190) at a first polarity and to second electrode surface (192) at a second (opposite) polarity, such that RF current flows between electrode surfaces (190, 192) and thereby through tissue captured between jaws (182, 184). In some versions, firing beam (195) serves as an electrical conductor that cooperates with electrode surfaces (190, 192) (e.g., as a ground return) for delivery of bipolar RF energy captured between jaws (182, 184). Electrical source (198) may be external to electrosurgical instrument (159) or may be integral with electrosurgical instrument (159) (e.g., in handpiece (160), etc.), as described in one or more references cited herein or otherwise. A controller (199) regulates delivery of power from electrical source (198) to electrode surfaces (190, 192). Controller (199) may also be external to electrosurgical instrument (159) or may be integral with electrosurgical instrument (159) (e.g., in handpiece (160), etc.), as described in one or more references cited herein or otherwise. It should also be understood that electrode surfaces (190, 192) may be provided in a variety of alternative locations, configurations, and relationships.

The lower side of first jaw (182) includes a longitudinally extending recess (not shown) adjacent to slot (186); while the upper side of second jaw (184) includes a longitudinally extending recess (not shown) adjacent to slot (188). FIG. 4 shows the upper side of first jaw (182) including a plurality of teeth serrations (194). It should be understood that the lower side of second jaw (184) may include complementary serrations that nest with serrations (194), to enhance gripping of tissue captured between jaws (182, 184) without necessarily tearing the tissue. Serrations (194) be constructed and operable in accordance with the teachings of U.S. patent application Ser. No. 13/235,660, published as U.S. Pat. Pub. No. 2012/0078247 on Mar. 29, 2012, and/or various other references that are cited and incorporated by reference herein.

With jaws (182, 184) in a closed position, shaft (170) and end effector (180) are sized and configured to fit through trocars having various inner diameters, such that electrosurgical instrument (159) is usable in minimally invasive surgery, though of course electrosurgical instrument (159) could also be used in open procedures if desired. Shaft (170) and end effector (180) may be constructed and operable in accordance with the teachings of U.S. patent application Ser. No. 13/235,660, published as U.S. Pat. Pub. No. 2012/0078247 on Mar. 29, 2012, and/or various other references that are cited and incorporated by reference herein.

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (e.g., PTC polymer, etc.), located adjacent to electrodes (190, 192) and/or elsewhere. Data from sensors may be communicated to controller (199). Controller (199) may process such data in a variety of ways. By way of example only, controller (199) may modulate or otherwise change the RF energy being delivered to electrode surfaces (190, 192), based at least in part on data acquired from one or more sensors at end effector (180). In addition or in the alternative, controller (199) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (199), and may simply provide a purely localized effect at end effector (180). For instance, a PTC thermistor bodies (not shown) at end effector (40) may automatically reduce the energy delivery at electrode surfaces (190, 192) as the temperature of the tissue and/or end effector (180) increases, thereby reducing the likelihood of overheating. In some such versions, a PTC thermistor element is in series with power source (198) and electrode surface (190, 192); and the PTC thermistor provides an increased impedance (reducing flow of current) in response to temperatures exceeding a threshold. Furthermore, it should be understood that electrode surfaces (190, 192) may be used as sensors (e.g., to sense tissue impedance, etc.). Various kinds of sensors that may be incorporated into electrosurgical instrument (159) will be apparent to those of ordinary skill in the art in view of the teachings herein. Similarly various things that can be done with data from sensors, by controller (199) or otherwise, will be apparent to those of ordinary skill in the art in view of the teachings herein. Other suitable variations for end effector (180) will also be apparent to those of ordinary skill in the art in view of the teachings herein.

C. Exemplary Firing Beam

As also seen in FIGS. 4-5, electrosurgical instrument (159) of the present example includes a firing beam (195) that is longitudinally movable along part of the length of end effector (180). Firing beam (195) is coaxially positioned within shaft (170), extends along the length of shaft (170), and translates longitudinally within shaft (170) (including articulation section (176) in the present example), though it should be understood that firing beam (195) and shaft (170) may have any other suitable relationship. Firing beam (195) includes a sharp distal blade (197), an upper flange (196), and a lower flange (not shown). Firing beam (195) may be constructed and operable in accordance with the teachings of U.S. patent application Ser. No. 13/235,660, published as U.S. Pat. Pub. No. 2012/0078247 on Mar. 29, 2012, and/or various other references that are cited and incorporated by reference herein. Distal blade (197) extends through slots (186, 188) of jaws (182, 184), with upper flange (196) being located above jaw (184) in a recess (not shown) and the lower flange (not shown) being located below jaw (182) in a recess (not shown). The configuration of distal blade (197), upper flange (196), and the lower flange (not shown) provides an "I-beam" type of cross section at the distal end of firing beam (195) and may be constructed and operable in accordance with the teachings of U.S. patent application Ser. No. 13/235, 660, published as U.S. Pat. Pub. No. 2012/0078247 on Mar. 29, 2012, and/or various other references that are cited and incorporated by reference herein.

Distal blade (197) is substantially sharp, such that distal blade will readily sever tissue that is captured between jaws (182, 184). Distal blade (197) is also electrically grounded in the present example, providing a return path for RF energy as described elsewhere herein. In some other versions, distal blade (197) serves as an active electrode. In addition or in the alternative, distal blade (197) may be selectively energized with ultrasonic energy (e.g., harmonic vibrations at approximately 55.5 kHz, etc.).

The "I-beam" type of configuration of firing beam (195) provides closure of jaws (182, 184) as firing beam (195) is advanced distally. In particular, flange (196) urges jaw (184) pivotally toward jaw (182) as firing beam (195) is advanced from a proximal position to a distal position, by bearing against a recess (not shown) formed in jaw (184). This closing effect on jaws (182, 184) by firing beam (195) may occur before distal blade (197) reaches tissue captured between jaws (182, 184). Such staging of encounters by firing beam (195) may reduce the force required to squeeze grip (164) to actuate firing beam (195) through a full firing stroke. In other words, in some such versions, firing beam (195) may have already overcome an initial resistance required to substantially close jaws (182, 184) on tissue before encountering resistance from the tissue captured between jaws (182, 184). Of course, any other suitable staging may be provided.

In the present example, flange (196) is configured to cam against a ramp feature at the proximal end of jaw (184) to open jaw (182) when firing beam (195) is retracted to a proximal position and to hold jaw (182) open when firing beam (195) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (195) is translated in the present example, it should be understood that other versions may provide independent movement of jaws (182, 184) and firing beam (195). By way of example only, one or more cables, rods, beams, or other features may extend through shaft (170) to selectively actuate jaws (182, 184) independently of firing beam (195). Such jaw (182, 184) actuation features may be separately controlled by a dedicated feature of handpiece (160). Alternatively, such jaw actuation features may be controlled by trigger (164) in addition to having trigger (164) control firing beam (195). It should also be understood that firing beam (195) may be resiliently biased to a proximal position, such that firing beam (195) retracts proximally when a user relaxes their grip on trigger (164).

D. Exemplary Operation

In an exemplary use, end effector (180) is inserted into a patient via a trocar. Articulation section (176) is substantially straight when end effector (180) and part of shaft (170) are inserted through the trocar. Articulation control (168) may then be manipulated to pivot or flex articulation section (176) of shaft (170) in order to position end effector (180) at a desired position and orientation relative to an anatomical structure within the patient. Two layers of tissue of the anatomical structure are then captured between jaws (182, 184) by squeezing trigger (164) toward pistol grip (162). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (159) is perpendicular to the longitudinal axis defined by end effector (180), etc.). In other words, the lengths of jaws (182, 184) may be oriented perpendicular to (or at least generally transverse to) the length of the blood vessel. As noted above, flanges (162, 166) cammingly act to pivot jaw (182) toward jaw (184) when firing beam (195) is actuated distally by squeezing trigger (164) toward pistol grip (162).

With tissue layers captured between jaws (182, 184) firing beam (195) continues to advance distally by the user squeezing trigger (164) toward pistol grip (162). As firing beam (195) advances distally, distal blade (197) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of upper flange (162) and the lower flange (not shown) immediately above and below jaws (182, 184), respectively, may help keep jaws (182, 184) in a closed and tightly clamping position. In particular, flanges (162, 166)

may help maintain a significantly compressive force between jaws (182, 184). With severed tissue layer portions being compressed between jaws (182, 184), electrode surfaces (190, 192) are activated with bipolar RF energy by the user depressing activation button (166). In some versions, electrodes (190, 192) are selectively coupled with power source (198) (e.g., by the user depressing button (166), etc.) such that electrode surfaces (190, 192) of jaws (182, 184) are activated with a common first polarity while firing beam (195) is activated at a second polarity that is opposite to the first polarity. Thus, a bipolar RF current flows between firing beam (195) and electrode surfaces (190, 192) of jaws (182, 184), through the compressed regions of severed tissue layer portions. In some other versions, electrode surface (190) has one polarity while electrode surface (192) and firing beam (195) both have the other polarity. In either version (among at least some others), bipolar RF energy delivered by power source (198) ultimately thermally welds the tissue layer portions on one side of firing beam (195) together and the tissue layer portions on the other side of firing beam (195) together.

In certain circumstances, the heat generated by activated electrode surfaces (190, 192) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (190, 192) may be activated with bipolar RF energy before firing beam (195) even begins to translate distally and thus before the tissue is even severed. For instance, such timing may be provided in versions where button (166) serves as a mechanical lockout relative to trigger (164) in addition to serving as a switch between power source (198) and electrode surfaces (190, 192).

While several of the teachings below are described as variations of instruments (10, 50, 101, 159), it should be understood that various teachings below may also be incorporated into various other types of devices. By way of example only, in addition to being readily incorporated into instruments (10, 50, 101, 159), various teachings below may be readily incorporated into the devices taught in any of the references cited herein, surgical staplers, surgical clip appliers, and tissue graspers, among various other devices. Other suitable devices into which the following teachings may be incorporated will be apparent to those of ordinary skill in the art in view of the teachings herein. Of course end effectors (16, 80, 150, 180) and surgical instruments (10, 50, 101, 159) may also include other configurations as will be apparent to one of ordinary skill in the art in view of the teachings herein.

IV. Exemplary Coupling Mechanisms for Modular Shafts and End Effectors

In some instances it may be useful to change between various shaft lengths and/or types of end effectors (16, 80, 150, 180) while using the same handle assembly (60, 120, 160). For instance, in some procedures, a large amount of tissue may need to be cut, requiring different length end effectors (80, 150, 180) and/or shafts for transmission assemblies (70, 102, 170). Such interchangeable shafts and/or end effectors (80, 150, 180) may permit a common handle assembly (60, 120, 160) to be used for various surgical procedures (e.g., short shafts for open surgery, long shafts for minimally invasive laparoscopic surgery, etc.). Moreover, changing out the shafts and/or the end effectors (80, 150, 180) while reusing the same handle assembly (60, 120, 160) may be more time and/or cost effective than using a new surgical instrument (50, 101, 159) with the different length shaft. By way of example only, such shafts and/or end effectors (80, 150, 180) may include color codes to distinguish the various lengths and/or types. In another instance, the handle assembly (60, 120, 160) may be configured to employ different types of end effectors, for instance, the handle assembly (60, 120, 160) may include components to operate an ultrasonic end effector (80, 150) and/or an RF end effector (180). Thus, changing the shafts and end effectors (80, 150, 180) with a common handle assembly (60, 120, 160) may conserve time and/or costs. Accordingly, various coupling mechanisms for coupling the modular shafts to the handle assemblies (60, 120, 160) are described below. It should be understood that in versions where an ultrasonic end effector (80) is used, at least part of transducer (100) may be integral with the shaft and end effector (80), and may thus be selectively coupled with handle assembly (60). Alternatively, transducer (100) may be integral with handle assembly (60) such that the shaft and end effector (80) are selectively coupled with transducer (100) when the shaft and end effector (80) are selectively coupled with handle assembly (60).

A. Exemplary Threaded Slip Nut

Figure 6A:
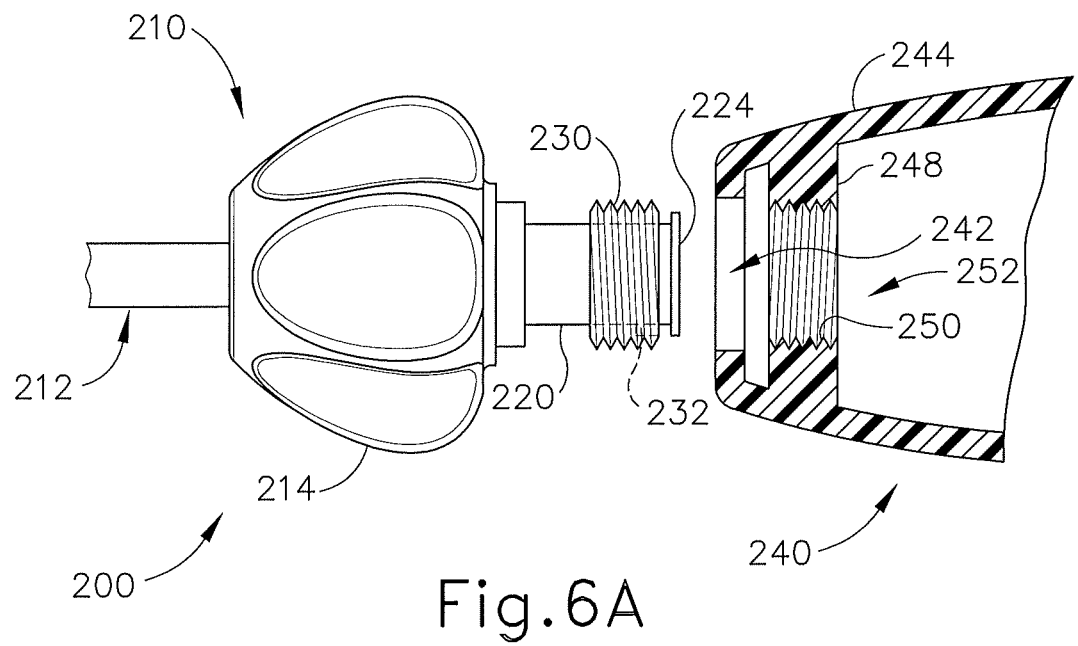
FIG. 6A depicts a side elevation view of a first exemplary coupling mechanism with a portion of a handle assembly in cross-section to show the interior thereof and showing a decoupled end effector assembly.
Figure 6B:
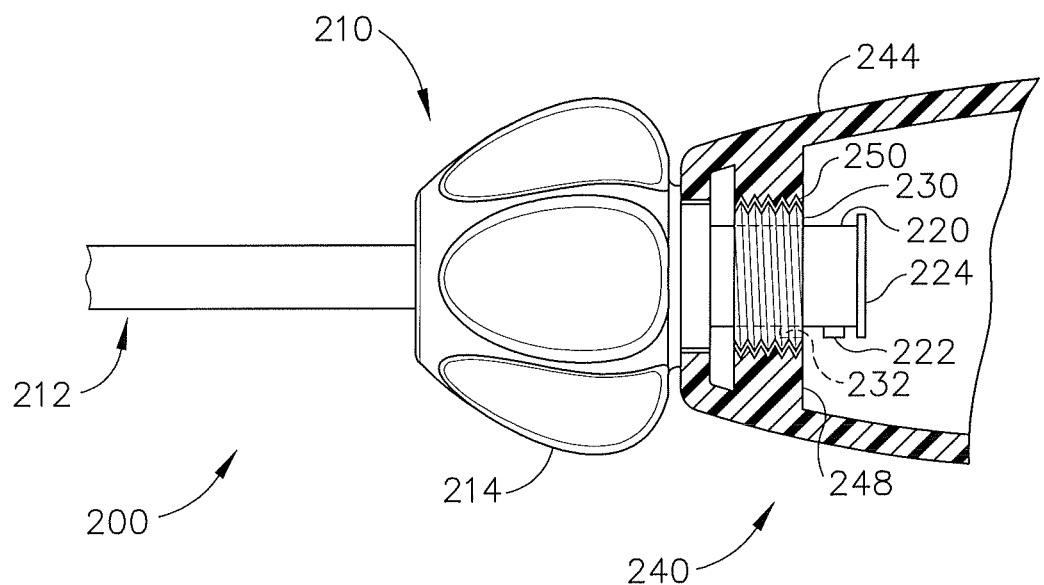
FIG. 6B depicts a side elevation view of the coupling mechanism of FIG. 6A showing the end effector assembly coupled to the handle assembly.

An exemplary coupling mechanism (200) comprises a threaded slip nut (230) disposed about a shaft (220) of an exemplary end effector assembly (210), shown in FIGS. 6A-6B. In the present example, end effector assembly (210) comprises a transmission assembly (212), a rotation knob (214), and a shaft (220) extending proximally relative to rotation knob (214). It should be understood that rotation knob (214) is merely optional and may be omitted. Rotation knob (214) is operable to rotate transmission assembly (212) relative to a handle assembly (240) and/or shaft (220). An end effector (not shown) is coupled to a distal end of transmission assembly (212). The end effector may include an ultrasonic end effector (80, 150), an RF end effector (180), and/or any other end effector or combination of end effectors as will be apparent to one of ordinary skill in the art in view of the teachings herein. Transmission assembly (212) is operable to communicate energy (e.g., ultrasonic vibrations, RF energy, and/or mechanical motion/force, etc.) from a source proximal to transmission assembly (212) to an end effector at the distal end of transmission assembly (212). In the instance of an ultrasonic end effector, such as end effector (80), an axial bore (not shown) through shaft (220) may permit mechanical coupling of transmission assembly (212) through shaft (220) to components within handle assembly (240), which may be configured in a similar manner to multi-piece handle assembly (60) described above. In the case of an RF end effector, such as end effector (180), the axial bore may permit a portion of transmission assembly (212) to extend at least partially through shaft (220). Transmission assembly (212) may include an inner slip ring connector that is electrically coupleable to a complementary slip ring connector on the interior of shaft (220) such that an electrical coupling from handle assembly (240) may be made to the end effector. In yet another alternative, a fluid coupling may also be made via the bore through shaft (220) and/or elsewhere on end effector assembly (210).

In the present example, a threaded slip nut (230) is slidably disposed about shaft (220). Threaded slip nut (230) includes a keyway (232) (shown in phantom) at a proximal end of threaded slip nut (230). It should be understood that keyway (232) may alternatively be located on a distal end of threaded slip nut (230). Keyway (232) of the present example only partially extends through threaded slip nut (230), though keyway (232) may alternatively extend completely through threaded slip nut (230). As shown in FIGS. 6A-6B, keyway (232) is configured to receive a keyed portion (222) of shaft (220). In the present example, keyed portion (222) of shaft (220) is located near a proximal end of shaft (220) and extends outwardly from shaft (220), though it should be understood that keyed portion (222) may alternatively be located distally near rotation knob (214) or at a midpoint of shaft (220). In one merely alternative example, keyed portion (222) may be slidable relative to shaft (220), such as by actuation of a slider to slide keyed portion (222) into keyway (232). Shaft (220) further comprises a proximal flange (224) located on the proximal end of shaft (220) and sized to prevent threaded slip nut (230) from sliding proximally off of shaft (220). As will be described below, keyed portion (222) is insertable into keyway (232) when a user desires to thread threaded slip nut (230) into internal threading (250) of handle assembly (240). Threaded slip nut (230) of the present example may then be slid distally on shaft (220) to disengage keyed portion (222) from keyway (232), thereby permitting shaft (220), rotation knob (214), and/or transmission assembly (212) to rotate freely relative to threaded slip nut (230) and/or handle assembly (240).

In some instance threaded slip nut (230) may be slidably disposed on an inner tube, such as an inner tubular actuating member described above. In such a configuration, threaded slip nut (230) may be configured to thread into a yoke, such as trigger yoke (185) described in U.S. Pat. Pub. No. 2011/0015660, entitled "Rotating Transducer Mount for Ultrasonic Surgical Instruments," published Jan. 20, 2011, now U.S. Pat. No. 8,461,744 issued on Jun. 11, 2013, the disclosure of which is incorporated by reference herein. A blade, such as blade (82) described above, may be coupled to a transducer, such as transducer (100) described above. The inner tubular actuating member may be actuated via the coupling of threaded slip nut (230) to the yoke. Accordingly, a clamp arm, such as clamp arm (84) described above, may be operable to clamp tissue against the blade.

In the present example, handle assembly (240) is shown having a distal aperture (242) formed within a casing (244) and configured to receive shaft (220) and threaded slip nut (230) of end effector assembly (210). Handle assembly (240) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, now U.S. Pat. No. 8,461,744 issued on Jun. 11, 2013, or of U.S. Pat. No. 6,500,176, entitled "Electrosurgical Systems and Techniques for Sealing Tissue," issued Dec. 31, 2002, the disclosures of which are incorporated by reference herein, and/or in any other suitable fashion. In the present example, handle assembly (240) includes a member (248) having internal threading (250) disposed about a member aperture (252). Internal threading (250) and threaded slip nut (230) are configured to thread together to secure end effector assembly (210) to handle assembly (240).

As shown in the sequence of FIGS. 6A-6B, threaded slip nut (230) of the present example is slid proximally such that keyed portion (222) of shaft (220) engages keyway (232) of threaded slip nut (230). With the rotational freedom of threaded slip nut (230) restricted by the engagement of keyed portion (222) and keyway (232), a user then threads threaded slip nut (230) into internal threading (250) of handle assembly (240). For instance, an L-shaped spacer tool may be used to urge threaded slip nut (230) proximally on shaft (220) against flange (224) while the user threads threaded slip nut (230) into internal threading (250). Alternatively, a user may manually urge threaded slip nut (230) proximally. Further still, a slider, as noted above, may engage a portion of threaded slip nut (230) to urge threaded slip nut (230) proximally. Of course, still other methods of urging threaded slip nut (230) proximally to engage keyed portion (222) and keyway (232) will be apparent to those of ordinary skill in the art in view of the teachings herein. For instance, a spring (not shown) may be disposed about shaft (220) distally of slip nut (230) and proximally of rotation knob (214), thereby biasing slip nut (230) proximally such that keyway (232) is engaged with keyed portion (222). When the user desires to rotate end effector assembly (210), the user grasps rotation knob (214) and pushes end effector assembly (210) proximally until keyed portion (222) disengages from keyway (232).

Once threaded slip nut (230) has been sufficiently threaded into internal threading (250) (for instance, a torque limiting tool may be used), end effector assembly (210) is slid proximally to disengage keyed portion (222) from keyway (232). End effector assembly (210) may be manually slid distally or, in one alternative, a spring (not shown) located between flange (224) and threaded slip nut (230) may urge end effector assembly (210) distally. In the instance of an ultrasonic instrument, shaft (220) of end effector assembly (210) may be threaded onto a horn of a transducer, such as transducer (100) described above. Such threading may occur prior to, contemporaneously with, or after the threading of threaded slip nut (230) into internal threading (250). Alternatively, in the instance of an RF instrument, shaft (220) may be coupled to one or more electrical connectors (not shown) to couple the end effector to a power source. As shown in FIG. 6B, end effector assembly (210) is effectively longitudinally secured to handle assembly (240) while permitting rotational movement of shaft (220), rotation knob (214), and/or transmission assembly (212). A user may then use the assembled surgical instrument for a procedure. When the user desires to decouple end effector assembly (210) from handle assembly (240), the user pulls end effector assembly (210) distally until keyed portion (222) of shaft (220) engages keyway (232) of threaded slip nut (230). Alternatively, the L-shaped spacer tool may be wedged between threaded slip nut (230) and rotation knob (214) to urge threaded slip nut (230) proximally. With keyed portion (222) and keyway (232) engaged, the user may then unscrew threaded slip nut (230) from internal threading (250), thereby decoupling end effector assembly (210) from handle assembly (240). A user may then couple a new end effector assembly (210) to handle assembly (240).

Of course other configurations for coupling mechanism (200) will be apparent to one of ordinary skill in the art in view of the teachings herein. For instance, threaded slip nut (230) may be located between flange (224) and another annular flange (not shown) of shaft (220). In this example, keyed portion (222) may be actuated radially outward from an initial position within a recess (not shown) of shaft (220) to a position where keyed portion (222) engages keyway (232) of threaded slip nut (230). For instance, keyed portion (222) may be actuated by a cam member coupled to a slider located on transmission assembly (212) and/or rotation knob (214). As will become apparent from the previous and later disclosures herein, various other electrical and/or mechanical coupling mechanisms and/or features may be used to substitute coupling mechanism (200), to modify coupling mechanism (200), or to combine with coupling mechanism (200).

V. Exemplary Smart Cartridge Assembly

Figure 7:
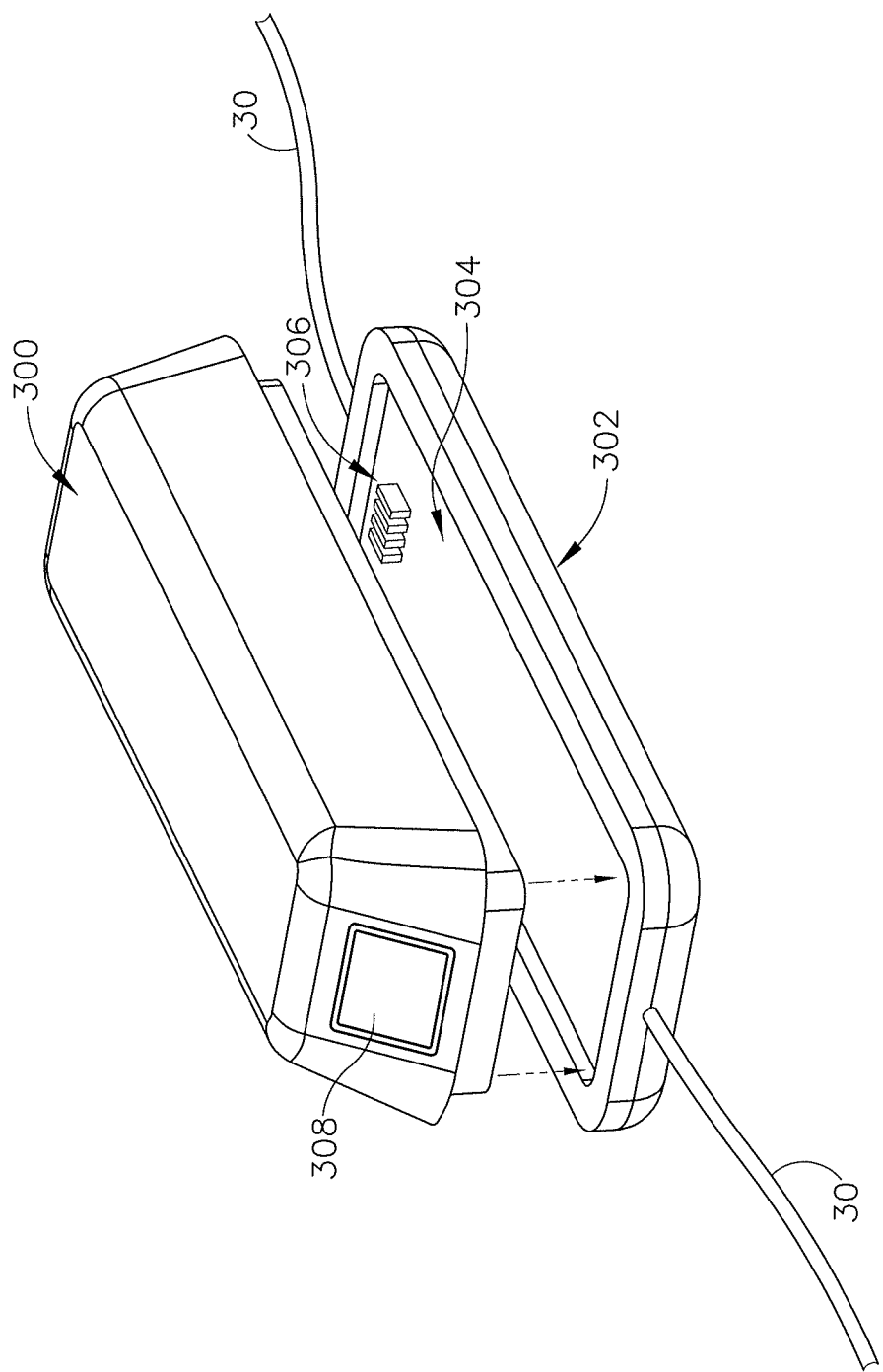
FIG. 7 depicts a perspective view of an exemplary cartridge and docking station.

A data module, such as smart cartridge (300) shown in FIG. 7, may be used in conjunction with removable end effectors (16, 80, 150, 180) and respective transmission assemblies (70, 102, 170) while using the same handle assembly (60, 120, 160) where it may be useful to change between various shaft lengths and/or end effector types, etc., as described above. Cartridge (300) may be similar to cartridge (26) shown in FIG. 1 and, similarly, be positioned between instrument (10, 24, 101) and generator (28), and connected to instrument (10, 24, 101) and generator (28) via cable (30). Cartridge (300) may be programmed to provide unique operating parameters as described above to a single use blade of end effector (16, 80, 150, 180) on a resterilizable handle (60, 120, 160), for instance. By way of example only, one cartridge (300) may be associated with one or more types of ultrasonic end effectors; while another cartridge (300) may be associated with one or more types of RF electrosurgical end effectors. The operating parameters may set, for instance, a range for or a maximum voltage to apply across adjacent tissue, and/or a range of or maximum forces to exert on jaws of end effectors (16, 80, 150, 180). By allowing for cartridge (300) to transmit the unique operating parameters rather than utilizing a transducer or generator for such transmission, a greater array of removable end effectors (16, 80, 150, 180) may be programmed and the cartridge may be used alongside one or more transducers, generators, and resterilizable handles (not shown, 60, 120, 160). In other words, the same "universal" generator, transducer, handle assembly, and/or other electronic/electrical components may be used for various end effector types, various surgical modalities (e.g., ultrasonic surgical modality, RF electrosurgical modality, powered stapling modality, etc.), and various surgical procedures (e.g., plastic surgery, orthopedic surgery, etc.) based on parameters established by cartridge (300).

FIG. 7 shows a docking station (302) including pocket (304). Pocket (304) is sized and shaped to receive an underside of cartridge (300). Pocket (304) includes connection portions or contacts (306), into which mutual connection prongs (not shown) from the underside of cartridge (300) connect. It should also be understood that cartridge (300) may have an inductive coupling with docking station (302) in addition to or in lieu of using contacts (306) for electrical communication. Cartridge (300) may be removably secured to docking station (302) via a magnetic connection, latches, clips, clamps, straps, and/or otherwise. Cartridge (300) include a memory chip, such as a read-only-memory (ROM) chip, that is capable of storing information such as desired procedural operating parameters, as described above. The chip may be an Electrically Erasable Programmable Read-Only Memory (EEPROM) chip, which may be used with a surgical instrument and/or computer as a type of non-volatile memory that stores data even when power is removed, such as date regarding device configuration and operating parameters. Docking station (302) may be an injection molded component that is sterilizable pre-use in a surgical procedure. The underside of docking station (302) may include a recessed opening into which to receive a portion of a drape covering a patient, so to secure docking station (302) within the vicinity of the patient during a surgical procedure. Additionally or alternatively, the underside of docking station (302) may comprise an adhesive to permit the attachment of docking station (302) to a patient-covering drape or other component in the vicinity of the patient during a procedure.

Cartridge (300) may be pre-programmed in a kit containing cartridge (300) and a unique blade and/or other component for a removable end effector (80, 140). While the example below references instrument (50) of FIG. 2, a similar use may occur with instrument (159) of FIG. 4. A program module within cartridge (300) which may comprise, for example, a memory chip, is programmed with a unique set of operating parameters associated with a particular type of end effector and/or a particular type of surgical procedure. A resterilizable handle (60), for example, is attached to a generator (28) via one or more cables (30). Cartridge (300) attaches to a first end of a first cable (30), a second end of which attaches to generator (28). Cartridge (300) also attached to a first end of a second cable (30), a second end of which attaches to instrument (50). The unique, single use blade may be loaded to end effector (80) of handle (60). Alternatively, a single use shaft (72) and end effector (80) assembly may be attached to handle (60). Particularly, the removable shaft and end effector assembly may be attached to and tightened against transducer (100). Generator (28) is then powered to send a signal to cartridge (300) to load the operating parameters data into the programmable, reusable handle (60). Instrument (50) may be used in a surgical procedure with the specific set of loaded operating parameters, as described above. As another variation, cartridge (300) may simply drive transducer (100), end effector (80), and/or other components in accordance with the parameters stored in cartridge (300), without having to load those parameters into another component. For example, handle (60) does not necessarily need to be programmable.

After the procedure, a first cartridge (300) may disconnected and removed from its connection to handle (60) along with the removable shaft and end effector assembly. If handle (60) has any type of memory, the memory associated with handle (60) may then be reset for reprogramming by a second cartridge (300) and second removable shaft and end effector assembly, where the second cartridge (300) has a different set of operating parameters from the first cartridge (300). The second removable shaft and end effector assembly may or may not have the same set of dimensions and/or surgical modality as the first removable shaft and end effector assembly. Cartridge (300) may integrally including program module (308) that includes a specific set of operating parameters and may connect to a receiver such as docking station (302) disposed between handle (60) of instrument (50) and generator (28), as described above and shown in FIGS. 1 and 7.

Figure 8:
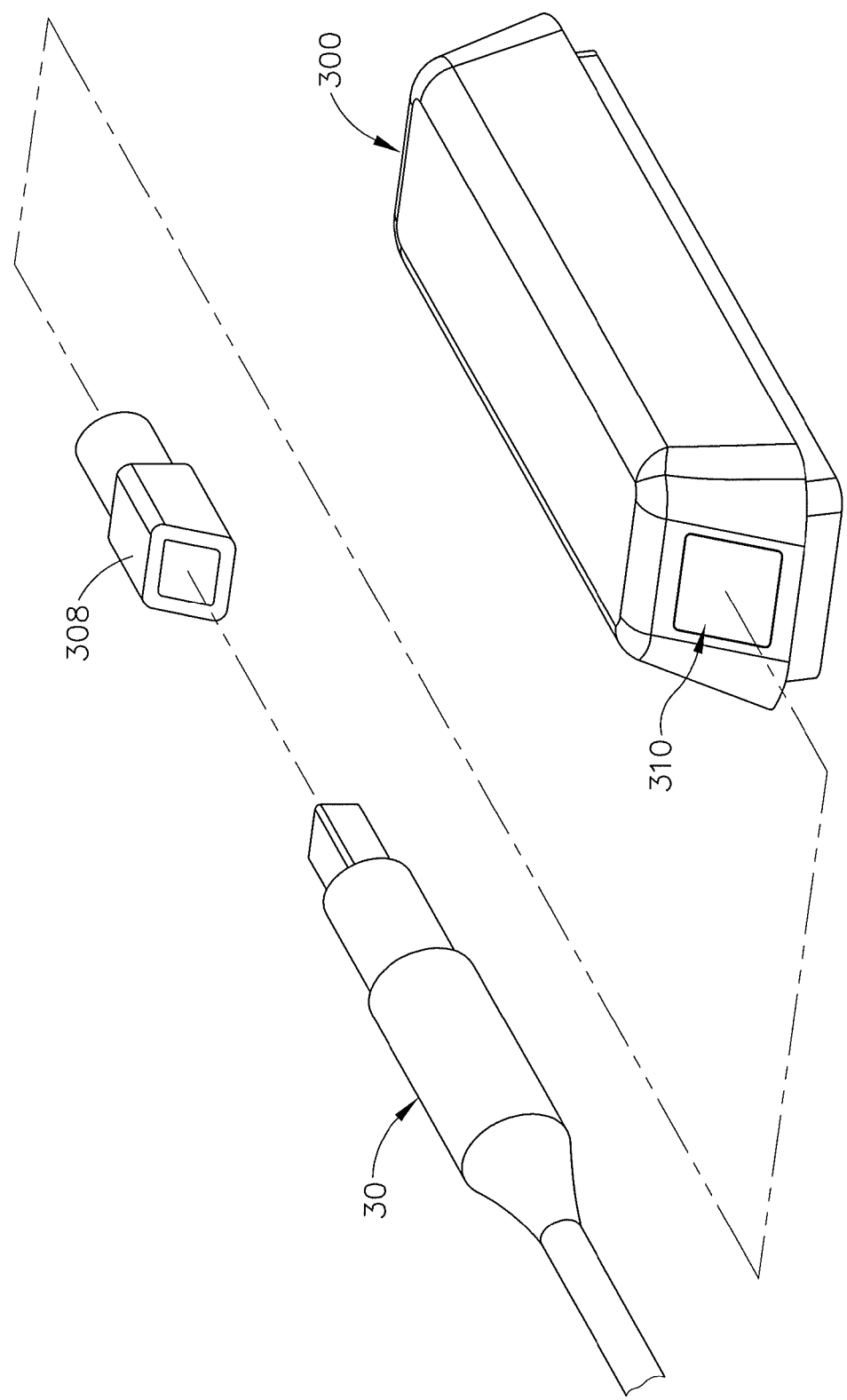
FIG. 8 depicts a perspective view of an exemplary cartridge receiving an exemplary cable connector.

Alternatively, program module (308) may be a separate component receivable into cartridge (300), as shown in FIG. 8. Cable (30), connected at one end to handle (60) for instance, connects at a second end to program module (308), which is then received into reception aperture (310) of cartridge (300). Program module (308) may include a magnetic feature to allow for a magnetic connection to cartridge (300). An aperture on an opposite surface of cartridge (300) may connect to a separate cable (30) leading to generator (28), for example; or such a cable may be integral with cartridge (300). Alternatively, cartridge (300) may couple only with a surgical instrument and not to a generator. Cartridge (300) may utilize alternative means of power, such as battery power from the device or from within cartridge (300), to transmit operating parameter information to the respective device.

Figure 9:
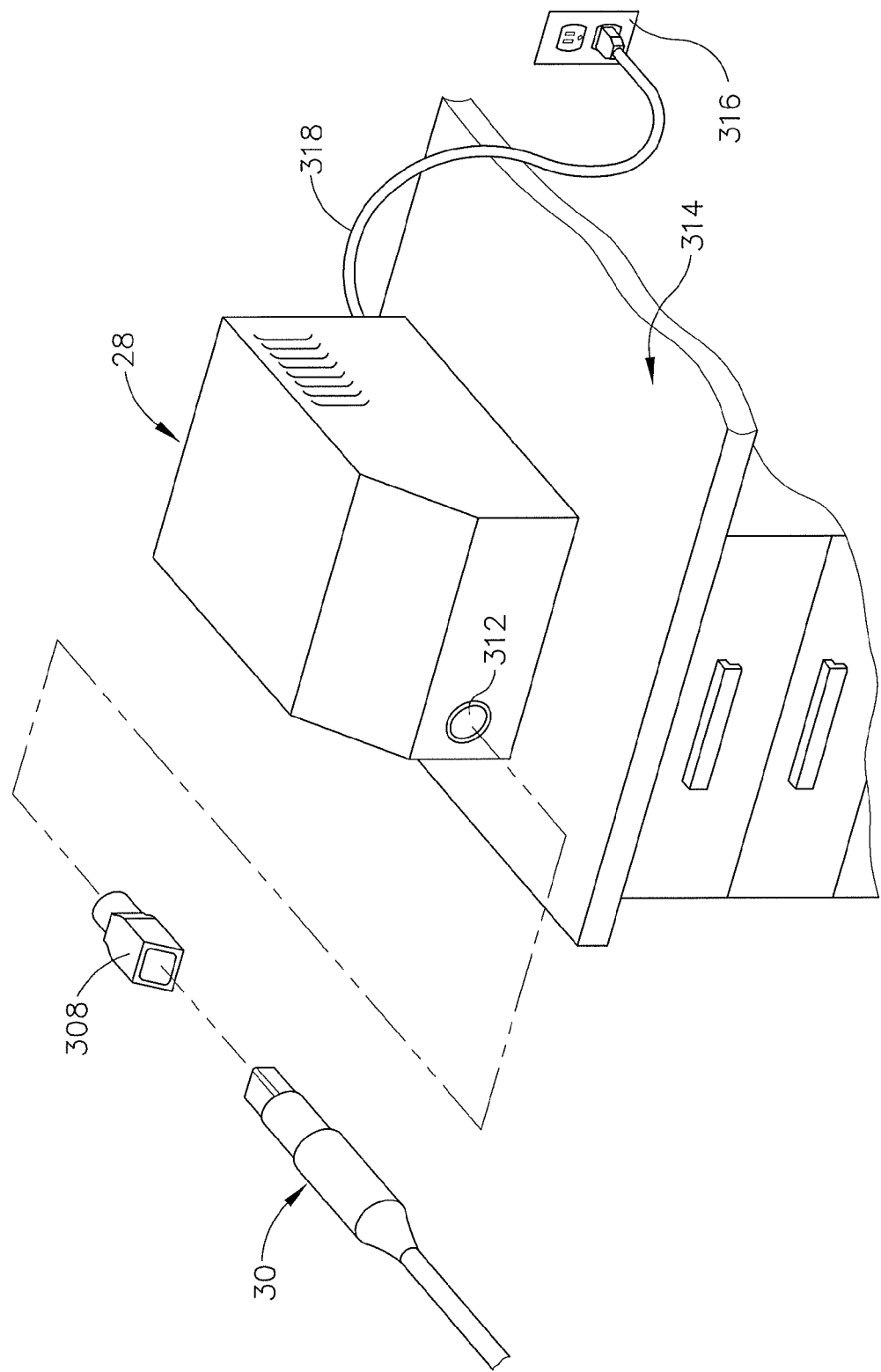
FIG. 9 depicts a perspective view of an exemplary cable connector for receipt in an exemplary generator.

In the alternative, where program module (308) is a separate component receivable into cartridge (300), program module (308) may be programmed within cartridge (300), or programmed before being coupled with cartridge (300) (e.g., cartridge (300) simply stores program module (308) and the blade together before use), removed from cartridge (300), and then plugged into port (312) of generator (28) as shown in FIG. 9 at a first end. A second end of program module (308) connects to an end of cable (30) via, for example, a magnetic connection. Program module (308) thus serves as an in-line adaptor between a conventional cable (30) and a conventional generator (28). While FIG. 9 shows a male portion of cable (30) that is receivable into a female portion of program module (308), the opposite type of connection is possible where a female portion of cable (30) is receivable into a male portion of program module (308). Similarly, while a male portion of program module (308) is shown as receivable within female port (312), the opposite type of connection is possible FIG. 9 also shows generator (28) resting on table (314) and receiving power from power source (316) via conduit (318), though any other suitable positioning or arrangement may be used.

Figure 10:
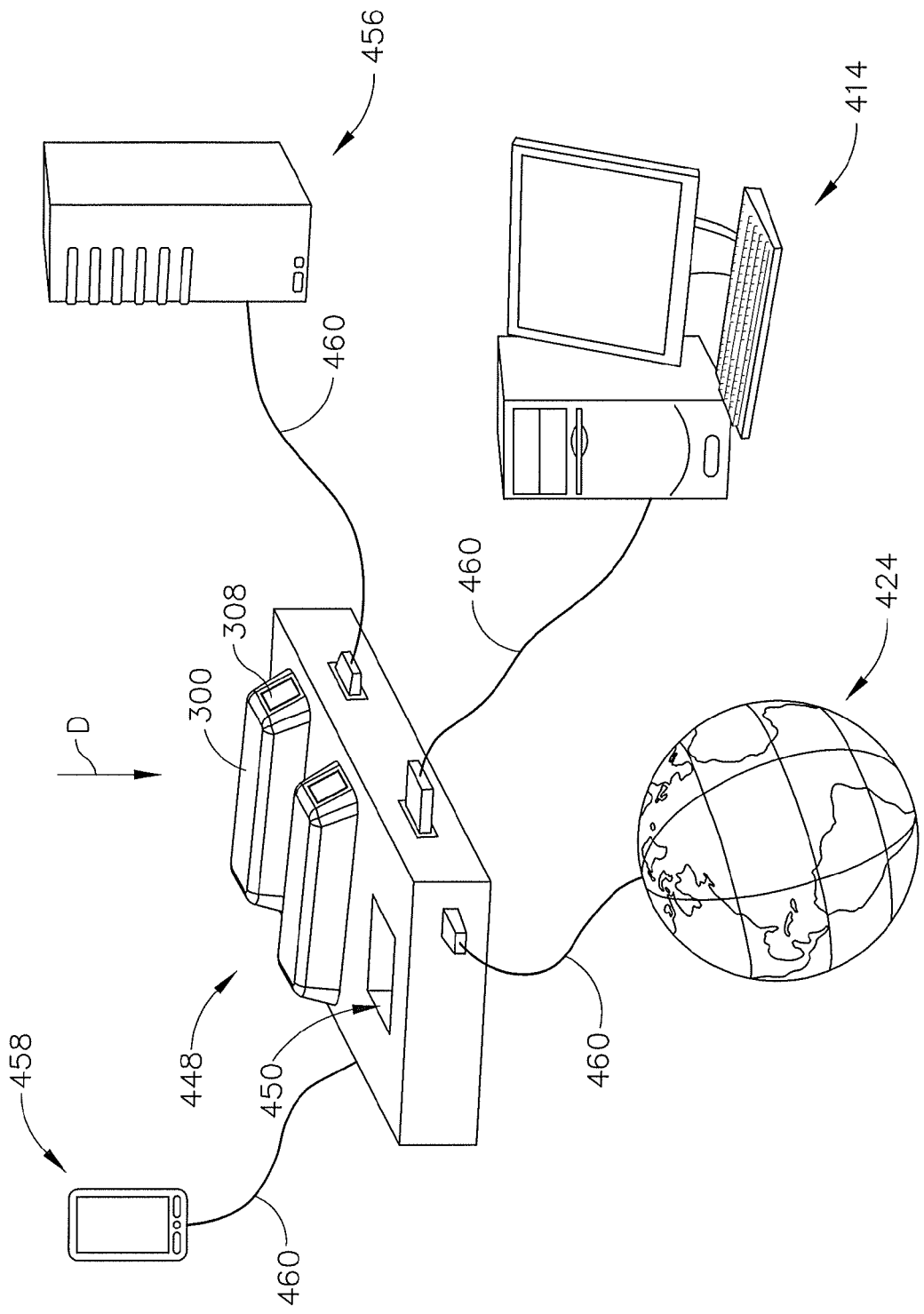
FIG. 10 depicts a perspective view of an exemplary cartridge and docking station assembly and various connections to which the docking station assembly may transmit information from the cartridge.

FIG. 10 shows an example in which cartridge (300) including program module (308) may be received in the direction of arrow (D) within reception port (450) in docking station assembly (448) to submit information retained during the surgical procedure to a variety of external sources via one or both of a wired and wireless connection. Wireless connections and information transmission from cartridge (300) may be used and operable in accordance with the teachings of U.S. patent application Ser. No. 13/276,725, published as U.S. Pat. Pub. No. 2012/0116367 on May 10, 2012, the disclosure of which is incorporated by reference herein. Of course, docking station assembly (448) could take various other forms and may simply comprise a direct USB coupling or other type of wired or wireless coupling, and/or other suitable type of coupling.

In use, a surgical instrument such as device (10) may record on program module (308) the type of instrument used and an amount of time (measureable in minutes, for example) that device (10) was used for during the procedure. Of course, any other type of data relating to the use and/or operation of device (10) may also be recorded on program module (408). Information from program module (408) may be downloaded and read by docking station assembly (448). The information may include device configuration data including a specific set of pre-determined operating parameters used with device (10). Additionally or alternatively, the information may pertain to, among other things, instrument performance, battery charge status, error codes, battery life, number of instrument uses, number of activations during the current use, power curve profiles or other parameters. The information may also or alternatively include performance parameters such as current and voltage supplied to either a transducer in an ultrasonic device or the end effector in an electrosurgical device throughout the entire procedure. The information may be used to determine usage for payment purposes (e.g., a customer paying for the amount of time the instrument was used during the procedure). Additionally or alternatively, the information may be relayed to a central storage device that would log a total use of the device(s) in the hospital and/or diagnose problems with device (10), among other possible actions as will be apparent to those of ordinary skill in the art in view of the teachings herein. In addition or in the alternative, the information may include data relating to any errors in the operation of device (10) and/or components of device (10).

The information may be sent to at least one of server (456), PC (414), World Wide Web (424) or other network, or a mobile device such as such as smartphone (458), shown as connected to docking station assembly (448) via wires (460). Smartphone (458) may be, but is not limited to being, an iPhone®. The mobile device may alternatively be, but is not limited to being, an iPad®. Both iPhone® and iPad® are registered trademarks of Apple, Inc. of Cupertino, Calif., or a Palm Pre®, a registered trademark of Palm Trademark Holding Company of Sunnyvale, Calif., or other similar mobile devices apparent to those of ordinary skill in the art in view of the teachings herein. Software programs can then be used to analyze the data on the memory card for use by the surgeon, the Operation Room ("OR") staff, biomedical researchers, or others. While the foregoing example relates to data being communicated from cartridge (300) to PC (414), World Wide Web (424), server (456), and/or smartphone (458), it should be understood that data, etc., may also be communicated from PC (414), World Wide Web (424), server (456), and/or smartphone (458) to cartridge (300) via docking station assembly (448) or via direct means such as a wireless or wired connection or other suitable connection directly to cartridge (300). For instance, PC (414), World Wide Web (424), server (456), and/or smartphone (458) may communicate operational parameters and/or firmware upgrades, etc., to cartridge (300).

Figure 11:
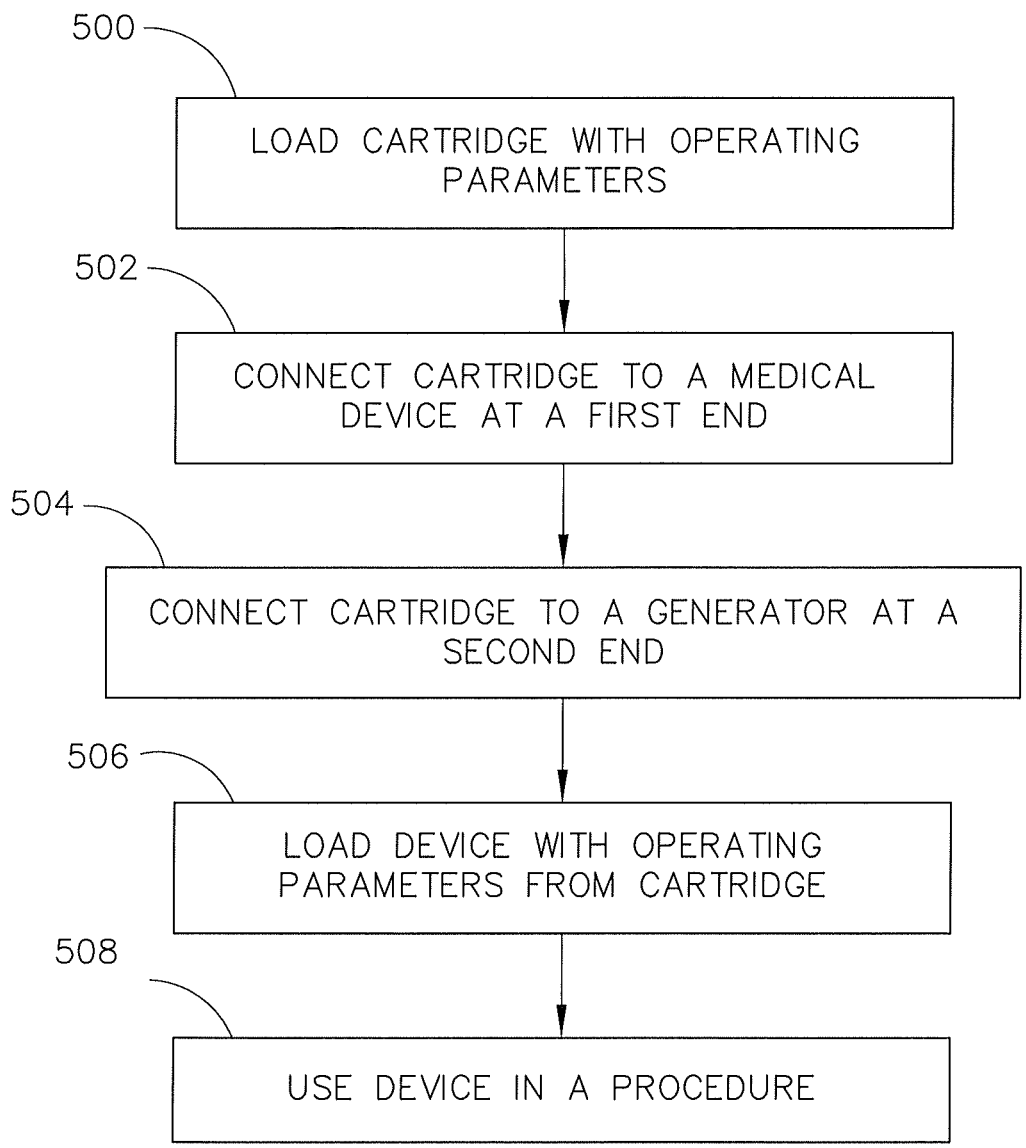
FIG. 11 depicts a flowchart of an exemplary process of loading an exemplary cartridge with operating parameters to transmit to a medical device and using the device.

As shown in FIG. 11 and as described above, in use, cartridge (300) and program module (308) is loaded (500) with one or more operating parameters such that the one or more operating parameters are stored within program module (308). Loaded cartridge (300) is then connected (502) to instrument (50) at a first end of cartridge (300). Cartridge (300) is connected (504) to generator (28) at a second end of cartridge (300). Instrument (50) is loaded (506) with the operating parameters transmitted from cartridge (300). Again, step (506) is merely optional, since some versions of cartridge (300) may be operable to directly modify or otherwise control the power from generator (28) based on the selected end effector and/or selected procedure. Loaded instrument (50) is used (508) in a surgical procedure such that a single use, removable end effector and shaft assembly operate per the operating parameters specified by cartridge (300). The used end effector and shaft assembly may also transmit information retrieved from the use and operation of instrument (50) during the procedure back to cartridge (300).

The EEPROM chip, described above, could be embedded in instrument (50) and include information specifying a maximum current set portion for generator (28). The specified current set point may be used to provide an enhanced, substantially optimum performance for a prospective surgeon-user group.

Figure 12:
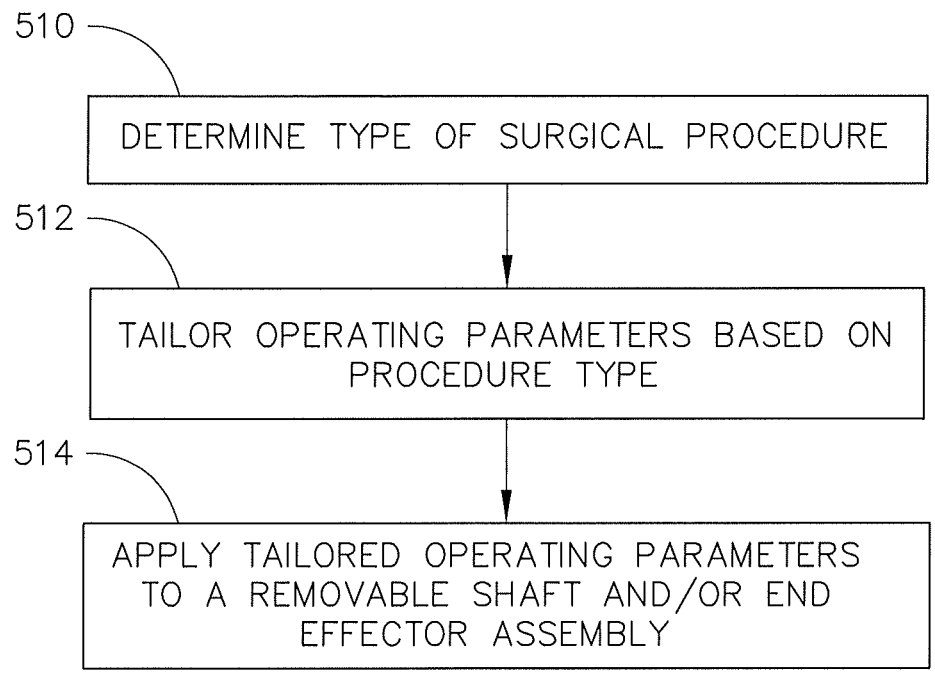
FIG. 12 depicts a flowchart of an exemplary process of tailoring operating parameters based on procedure type.

As shown in FIG. 12, a type of procedure may be determined (510). The procedure may be, for example, a plastic surgery or an orthopedic procedure. The operating parameters associated with a given cartridge (300) may be tailored (512) based on the type of procedure. A surgeon may desire a different tradeoff between cut speed and hemostatis than a certain instrument (50) may otherwise provide. For instance, in some settings a cut speed rate associated with an instrument may tend to increase as a hemostatis rate associated with a first pass of the instrument decreases. By way of example only, this relationship may be quantified with regression coefficients exceeding 50%; in some instances higher than 70%. The tradeoff is a function of blade displacement from a shaft and end effector assembly, controllable via changing a current set point of transducer (28). By changing a current set point in transducer (28) to be unique for a specific removable shaft and end effector assembly, and by specifying a type of surgical procedure, the blade displacement may be adjusted to achieved a desired tradeoff area between cut speed and hemostatis. A plastic surgeon, for instance, may cut through smaller vessels than an orthopedic surgeon and may desire a faster hemostatis rate even at the tradeoff of a decreased cut speed. An orthopedic surgeon, by contrast, may be cutting through more dense tissue including more ligaments and larger blood vessels and may desire an increased cut speed even at a tradeoff of a decreased hemostasis rate. The tailored operating parameters may then be transmitted or applied (514) by a cartridge (300) to a removable shaft and/or removable end effector assembly, as described above.

Figure 13:
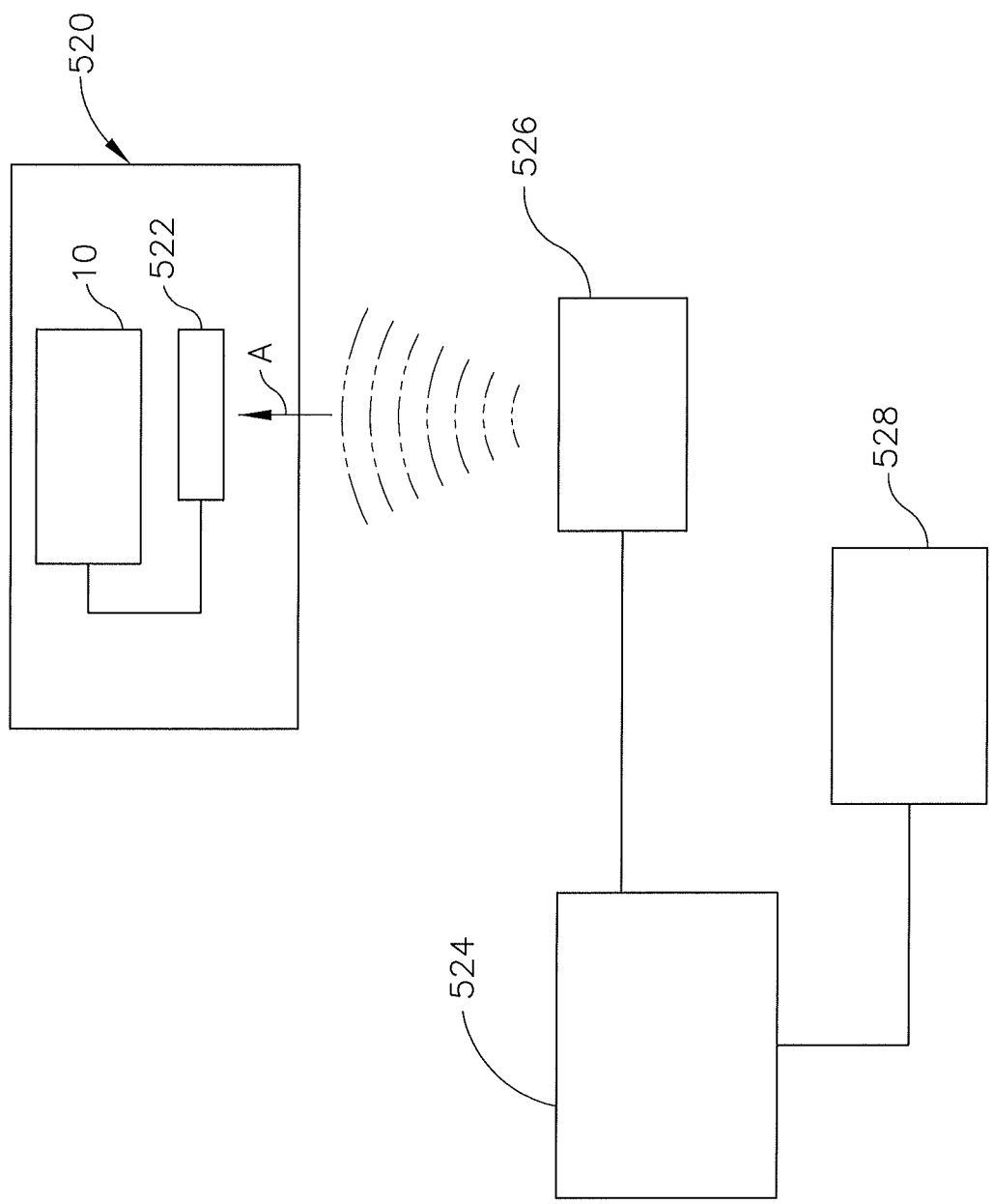
FIG. 13 depicts a schematic view of the transmission of information to a medical device contained within a sterilized packaging.

FIG. 13 shows a schematic view of an example of transmission of information to device (10) contained within a sterilized packaging unit (520). Device (10) includes an information receiving device such as radiofrequency (RF) receiver (522) which may be included within or separate from sensor

(20) of FIG. 1. Device (10) of this example is a multi-function surgical instrument that is operable to perform various surgical modalities and/or to be used in various kinds of surgical procedures, depending on operational parameters used to program device (10). Unit (520) may be comprised of a plastic or polyester material such as a polyethylene terephthalate (PET) modified by adding cyclohexane dimethanol (CHDM) to the polymer backbone in place of ethylene glycol, which results in a clear amorphous thermoplastic known as PETG that is able to be injection molded or sheet extruded; or may be comprised of other suitable materials as apparent to those skilled in the art in view of the teachings herein. A controller or programmer (524) comprises an information transmitting station, such as RF docking station (526), and a label generator (528). Station (526) wirelessly transmits information from programmer (524) as shown by arrow (A) to RF receiver (522) of device (10). Information may be transmitted via means such as, for example, the use of RF wireless (e.g., using the protocol of Bluetooth®, a registered trademark of Bluetooth Sig, Inc. of Kirkland, Wash.), and/or infrared technologies. Station (526) may receive unit (520) or may wirelessly transmit information to a unit (526) when it is a certain distance away from station (526), for instance; or upon receiving a signal to transmit information to one or more devices (10) within a specified vicinity or distance. Programmer (524) submits a selected portion of that information to label generator (528).

Figure 14:
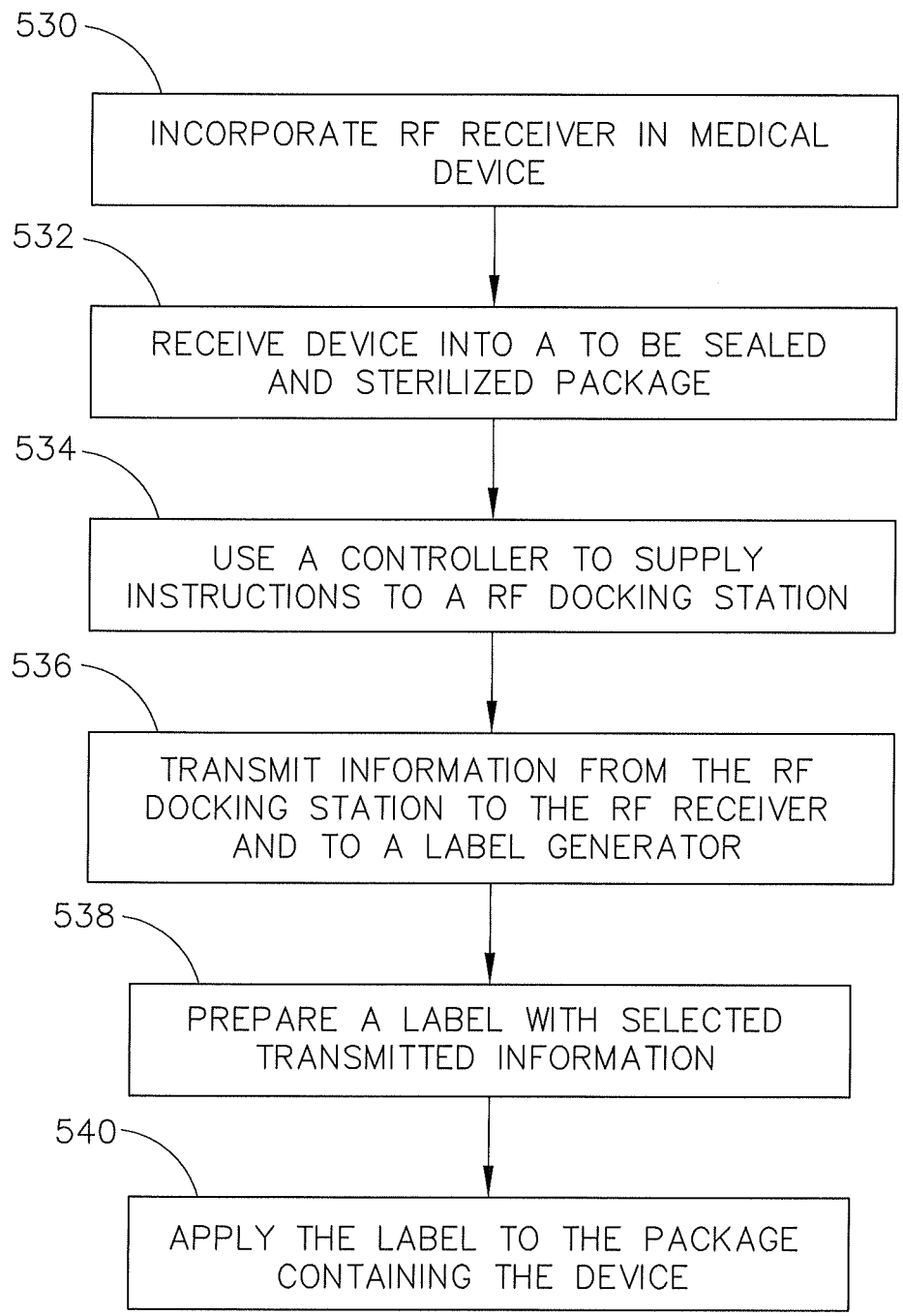
FIG. 14 depicts a flowchart of an exemplary process of transmitting information to a medical device contained within a sterilized packaging.

FIG. 14 shows an exemplary process associated with the use of programmer (524) in FIG. 13. RF receiver (522) is incorporated (530) into device (10). Device (10) is received (532) into a packaging unit (520) that is to be sealed and sterilized. Unit (520) is sealed and sterilized, and sent to a hospital or other site where device (10) will eventually be used. At the hospital or similar site, programmer (524) is used (534) to supply operating parameters to RF docking station (526), as described above. The operating parameter information is transmitted (536) from RF docking station (526) to RF receiver (522) and to label generator (528), as described above. A label (not shown) is prepared (538) or printed to show a portion of or all of the information transmitted to device (10). For instance, the label may indicate that device (10) is programmed for use in a plastic surgery procedure. The label is then applied (540) to unit (520) containing device (10) such that a user may know what operating parameters have been loaded to device (10). Thus, programmer (524) enables surgeons and other hospital personnel to easily program a relatively "universal' instrument (10) on an ad hoc basis based on present surgical needs and/or based on a particular surgeon's preferences.

For the foregoing examples, it should be understood that the handle assemblies and/or end effectors may be reusable, autoclavable, and/or disposable. For instance, the foregoing end effectors may be disposable while the handle assemblies are reuseable and/or autoclavable. In addition, if internal power sources are used with the foregoing handle assemblies, the internal power sources may be rechargeable. For instance, the handle assemblies may be recharged using a plug in recharge, by removing and recharging the batteries, by induction, and/or by any other method as will be apparent to one of ordinary skill in the art in view of the teachings herein. Furthermore, alignment features or guides may be included to aid in the alignment and coupling of the end effectors with handle assemblies. Such guides may help prevent damage to the end effector and/or handle assembly during the assembly of the surgical instrument.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," issued Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
(a) an instrument body, the instrument body comprising an instrument power connector, wherein the body is operable to communicate with different kinds of end effector assemblies;
(b) a modular end effector assembly, wherein the modular end effector assembly is operable to removably couple with the body;
(c) a power source operable to drive the end effector, the power source comprising a power source connector; and
(d) a detachable control module associated with the modular end effector assembly, wherein the detachable control module is operable to control delivery of power from the power source to the end effector assembly, the program module comprising an input power connector and an output power connector;
wherein the detachable control module comprises a cartridge and a program module programmed to store a set of operating parameters associated with the end effector assembly;
wherein the instrument power connector is adapted to be coupled with the output power connector; and
wherein the power source connector is adapted to be coupled with the input power connector.

2. The surgical instrument of claim 1, wherein the power source comprises a generator, wherein the detachable control module is disposable between the instrument body and the generator.

3. The surgical instrument of claim 2, wherein the detachable control module is configured to receive power from the generator, wherein the detachable control module is configured to transmit one or more stored operating parameters to a memory device of the surgical instrument upon receipt of power from the generator.

4. The surgical instrument of claim 3, wherein the detachable control module is removable from the position between the surgical instrument and the generator, and wherein the detachable control module is operable to remove the one or more stored operating parameters from the memory device of the surgical instrument upon decoupling of the detachable control module from the generator.

5. The surgical instrument of claim 1, wherein the program module comprises an EEPROM chip.

6. The surgical instrument of claim 1, wherein the power source comprises a generator, wherein the program module is integral with the cartridge, wherein the cartridge is configured to couple with a docking station disposed between the surgical instrument and the generator, wherein the docking station is connected to each of the surgical instrument and the generator via a respective electrical conduit.

7. The surgical instrument of claim 1, further comprising one or more electrical conduits, wherein the program module is removable from the cartridge and is operable to attach at least one electrical conduit connected to the surgical instrument.

8. The surgical instrument of claim 1, further comprising one or more electrical conduits, wherein the program module is removable from the cartridge and is operable to couple at least one of the electrical conduits with the power source.

9. The surgical instrument of claim 8, wherein the program module is configured to attach the at least one electrical conduit to the power source via magnetic forces.

10. The surgical instrument of claim 1, wherein the end effector assembly comprises an ultrasonic end effector assembly including an ultrasonic blade.

11. The surgical instrument of claim 1, wherein the end effector assembly comprises an RF electrosurgical end effector assembly.

12. The surgical instrument of claim 1, wherein the modular end effector assembly is operable to detachably couple to the body via a threaded connection.

13. The surgical instrument of claim 1, further comprising a docking station assembly, wherein the detachable control module is attachable to the docking station assembly.

14. The surgical instrument of claim 13, wherein the docking station assembly is in communication with a computer via a wireless connection, and wherein the detachable control module is configured to at least one of transmit or receive a wireless signal including data to or from the computer when the detachable control module is coupled with the docking station assembly.

15. The surgical instrument of claim 1, wherein the input power connector is a first end of the program module, and the output power connector is a second end of the program module.

16. The surgical instrument of claim 1, wherein the set of operating parameters comprises a current set point and a procedure type, and wherein a cutting speed of the surgical instrument is determined based at least in part upon the current set point and the procedure type.

17. The surgical instrument of claim 1, wherein the instrument power connector comprises a first length of external cable, and wherein the power source connector comprises a second length of external cable.

18. A surgical instrument comprising:
(a) a handle assembly, wherein the handle assembly is operable to communicate with different kinds of end effector assemblies, wherein the handle assembly comprises a pistol grip and a trigger pivotable toward and away from the pistol grip, the handle assembly comprising an instrument power connector;
(b) a first modular end effector assembly, wherein the modular end effector assembly is operable to removably couple with the handle assembly;
(c) a power source operable to drive the end effector, the power source comprising a power source connector;
(d) a first detachable control module associated with the first modular end effector assembly, wherein the first detachable control module stores a first set of operating parameters configured to operate the first modular end effector assembly, the first detachable control module comprising a first input power connector and a first output power connector;
(e) a second module end effector assembly, wherein the second modular end effector assembly is operable to removably couple with the handle assembly; and
(f) a second detachable control module associated with the second modular end effector assembly, wherein the second detachable control module stores a second set of operating parameters configured to operate the second modular end effector assembly, the second detachable control module comprising a second input power connector and a second output power connector;
wherein the instrument power connector is adapted to be coupled with the first output power connector and the second output power connector;
wherein the power source connector is adapted to be coupled with the first input power connector and the second input power connector;
wherein a user determines a set of operating parameters for a modular end effector assembly by attaching a detachable control module, the detachable control module selected from the list consisting of the first detachable control module and the second detachable control module.

19. A surgical instrument comprising:

(a) an instrument body, wherein the body is operable to communicate with different kinds of end effector assemblies, the instrument body comprising an instrument power connector;

(b) a modular end effector assembly, wherein the modular end effector assembly is operable to removably couple with the body;

(c) a power source operable to drive the end effector, the power source comprising a power source connector;

(d) a detachable control module associated with the modular end effector assembly, the detachable control module comprising an input power connector and an output power connector, wherein the detachable control module stores a set of operating parameters; and (e) a docking station assembly, wherein the detachable control module is attachable to the docking station assembly;

wherein the instrument power connector is adapted to be coupled with the output power connector;

wherein the power source connector is adapted to be coupled with the input power connector;

wherein the modular end effector assembly is operable based upon the set of operating parameters; and wherein the docking station assembly is operable to modify the set of operating parameters when the detachable control module is attached to the docking station assembly.

* * * * *